US006191115B1

(12) United States Patent
Haviv et al.

(10) Patent No.: US 6,191,115 B1
(45) Date of Patent: Feb. 20, 2001

(54) C-TERMINUS MODIFIED HEPTAPEPTIDE LHRH ANALOGS

(75) Inventors: Fortuna Haviv, Deerfield; Wesley J. Dwight, Evanston, both of IL (US); Charles J. Nichols, Greendale, WI (US); Jonathan Greer, Chicago, IL (US)

(73) Assignee: Abbott Laboratories, Abbott Park, IL (US)

( * ) Notice: Under 35 U.S.C. 154(b), the term of this patent shall be extended for 0 days.

(21) Appl. No.: 09/232,425

(22) Filed: Jan. 15, 1999

Related U.S. Application Data

(60) Provisional application No. 60/096,202, filed on Aug. 12, 1998, now abandoned.

(51) Int. Cl.$^7$ .......................... A61K 38/00; A61K 38/04; C07K 16/00
(52) U.S. Cl. ............................. 514/16; 530/329; 530/313
(58) Field of Search .............................. 514/16; 530/329, 530/313

(56) References Cited

U.S. PATENT DOCUMENTS

| 4,087,416 | | 5/1978 | Tinney et al. | 260/112.5 |
| 4,800,191 | * | 1/1989 | Schally et al. | 514/15 |
| 5,110,904 | | 5/1992 | Haviv et al. | 530/313 |
| 5,140,009 | * | 8/1992 | Havivi et al. | 514/16 |
| 5,413,990 | * | 5/1995 | Haviv et al. | 514/15 |
| 5,502,035 | * | 3/1996 | Haviv et al. | 514/15 |
| 5,843,901 | * | 12/1998 | Roeske | 514/15 |

FOREIGN PATENT DOCUMENTS 0417454    3/1991   (EP) .

OTHER PUBLICATIONS

Janecka, et al., "Reduced–Size Antagonists of Lutenizing Hormone–Releasing Hormone Active in vitro" *Journal of Medicinal Chemistry*, vol. 38 (1995), pp. 2922–2924.

Janecka, et al., "The Structural Features of Effective Antagonists of the Luteinizing Homrone Releasing Hormone", *Amino Acids*, vol. 6 (1994), pp. 111–130.

Chang, et al., "Studies on Analogs of the Luteinizing Releasing Hormone Towards Elucidation of the Release Mechanism", *Biochemical and Biophysical Research Communications*, vol. 47 (1972), pp. 1256–1261.

Fertility and Sterility, vol. 22, No. 11, (Nov. 1971), pp. 703–721; Schally, et al., Hypothalamic Follicle–Stimulating Hormone (FSH) and Luteinizing Hormone (LH–Regulating Hormone: Structure, Physiology, and Clinical Studies.

Science, vol. 202, (Oct. 1978), Andrew V. Schally, pp. 18–28, "Aspects of Hypothalamic Regulation of the Pituitary Gland".

Haviv et al., Effect of N–Me Tyr 5 Substitution in Luteinizing Hormone–Releasing Hormone antagonists, J. Med. Chem. vol. 36, No. 7, pp. 928–933, 1993.*

Haviv et al., Effect of N–Methyl Substitution of the Peptide Bond in Luteinizing Homrone–Releasing Hormone Agonists J. Med. Chem. vol. 36, No. 3, pp. 363–369, 1993.*

Hawley's Condensed Chemical Dictionary, 13th ed., John Wiley and Sons, Inc. p. 925, 1997.*

* cited by examiner

*Primary Examiner*—F. T. Moezie
(74) *Attorney, Agent, or Firm*—Dugal S. Sickert

(57) ABSTRACT

The present invention relates to a class of heptapeptide analogs of LHRH. These compounds are useful in the treatment of disease conditions which are mediated by reproductive hormones, including benign prostate hyperplasia, prostate tumors, breast and ovaries tumors, cryptorchidism, hirsuitism, gastric motility disorders, dysmenorrhea, and endometriosis.

13 Claims, No Drawings

C-TERMINUS MODIFIED HEPTAPEPTIDE LHRH ANALOGS

CLAIM OF PRIORITY

This application claims the benefit of U.S. Provisional Application No. 60/096,202, filed Aug. 12, 1998 now abandoned.

TECHNICAL FIELD OF INVENTION

The present invention relates to novel analogs of LHRH. The novel analogs provide heptapeptides truncated from the C-terminus of LHRH antagonist peptides. The invention also relates to processes for preparing the disclosed compounds, pharmaceutical compounds containing such compounds, and use of such compounds for modulating levels of sex hormones in male or female mammals.

BACKGROUND OF THE INVENTION

Luteinizing hormone releasing hormone (LHRH) is released from the hypothalamus and binds to a receptor on the anterior pituitary gland causing the release of gonadotropin hormones. The gonadotropin hormones, luteinizing hormone (LH) and follicle-stimulating hormone (FSH), secreted from the anterior pituitary gland, regulate fundamental reproductive processes, such as ovarian release and gamete maturation. These play a major role in regulating the synthesis of the steroidal reproductive hormones from the gonads, ie. estrogen and progesterone in females and testosterone in males.

The ongoing system of feedback between hypothalamus, the anterior pituitary gland, and the gonads modulates the fundamental processes related to the reproductive cycle. The feedback process, described by A. V. Schally et al., *Fertility and Sterility*, 22:11 (1971), provides a web of complex relationships related to reproductive functions. Pulsatile release of the gonadotropin hormones controls levels of steroidal hormone circulating in the mammalian reproductive cycle. Manipulation of the release of these hormones provides an avenue for the design of novel agents useful in treating various conditions related to dysfunction of the reproductive cycle and hormone dependent diseases. Several agonists of natural LHRH have been shown to be clinically useful.

Natural mammalian releasing hormone LHRH isolated and purified from porcine and human hypothalami has been characterized as having the sequence:

(Pyro)Glu-His-Trp-Ser-Tyr-Gly-Leu-Arg-Pro-Gly-$NH_2$ as described in A. V. Schally, *Science*, 202:6 (1978). Substitutions and derivatizations of amino acyl residues have been developed to achieve novel compounds useful in treating various disorders related to mammalian reproductive systems.

Synthetic analogs of LHRH have been described in a number of U.S. patents for exhibiting activity as LHRH agonists or as antagonists of LHRH. For the most part, these compounds contain nine or ten amino acyl residues, substituting naturally-occurring or non-naturally occurring amino acid residues at one or more positions in the natural sequence of LHRH. U.S. Pat. No. 5,110,904 describes nonapeptide and decapeptide LHRH antagonists wherein the nitrogen atom of at least one of the amide bonds has been alkylated. The decapeptide and undecapeptide analogs described in U.S. Pat. No. 5,502,035 have an acyl-substituted N-terminal nitrogen atom.

Truncated peptide compounds have been developed as series of smaller peptide analogs also exhibiting biological activity and having the added advantage of possibly improved oral bioavailability. These reduced-size peptides, described in U.S. Pat. No. 5,140,009, exhibit effective LHRH agonist or antagonist activity. They are "pseudo" hexapeptide, heptapeptide, octapeptide and nonapeptide analogs of LHRH, which have 1 to 3 amino acids eliminated from the N-terminus of a decapeptide antagonist sequence to achieve activity as LHRH antagonists. Distinctively, the peptides described in this invention have the 10 to 8 amino acids eliminated from the C-terminus. Copending U.S. application Ser. No. 09/373,180 discloses and claims a class of pentapeptide LHRH analogs wherein the 1 to 3 amino acids are eliminated from the N-terminus and the 10 to 8 amino acids from the C-terminus of a decapeptide LHRH antagonist.

The development of synthetic LHRH antagonists truncated from the C-terminus having biological activity provides novel compounds for treatment of hormone dependent diseases in male and female mammals. Smaller synthetic peptide sequences provide significant advantages when compared to decapeptide LHRH analogs. These LHRH antagonists are useful in the treatment of a variety of clinical condition in which the suppression of sex steroids plays a major therapeutic role, including delay of puberty, treatment of benign prostatic hyperplasia, palliative treatment or remission of hormonal-dependent tumors of breast and ovaries, palliative treatment or remission of hormonal-dependent tumors of the prostate, the treatment of cryptorchidism, hirsutism in women, gastric motility disorders, dysmenorrhea, and endometriosis.

SUMMARY OF THE INVENTION

The compounds of the invention comprise a peptide of the formula:

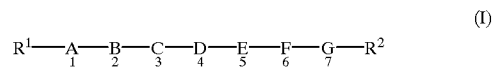

(I)

or a pharmaceutically acceptable salt, ester, or prodrug thereof, wherein:

$R^1$ is of the formula $R^3(C=O)—$, wherein $R^3$ is lower alkyl;

A is an amino acyl residue selected from the group consisting of:
3-(2-naphthyl)-D-alanyl;
[3-(4-chloro)]-D-phenylalanyl; and
sarcosyl;

B is an amino acyl residue selected from the group consisting of:
3-(1-naphthyl)-D-alanyl; and
[3-(4-chloro)]-D-phenylalanyl;

C is an amino acyl residue selected from the group consisting of:
3-(3-pyridyl)-D-alanyl; and
3-(1-naphthyl)-D-alanyl;

D is seryl;

E is an acyl group selected from the group consisting of:
arginyl;
(N-epsilon-nicotinyl)lysyl;
N-methylphenylalanyl;
[4-(3-amino-1,2,4-triazol-5-yl)]phenylalanyl;
[4-(3-amino-1,2,4-triazol-5-yl)]-N-methylphenylalanyl;
[4-(N-acetyl)]-N-methylphenylalanyl;
[4-(N-nitro)]-N-methylphenylalanyl;

[4-(N-acetyl)]-phenylalanyl;
tyrosyl;
N-methyltyrosyl; and
1,2,3,4-tetrahydroisoquinoline-3-carbonyl;

F is an amino acyl residue selected from the group consisting of:
D-arginyl;
D-asparaginyl;
D-citrullyl;
D-glutamyl;
D-homocitrullyl;
D-2-amino-6-$N^G,N^G$-diethylguanidinohexanoyl;
(N-epsilon-nicotinyl)-D-lysyl;
[4-(3-amino-1,2,4-triazol-5-yl)]-D-phenylalanyl;
[4-(N-acetyl)]-D-phenylalanyl; and
D-tryptyl;

G is an amino acyl residue selected from the group consisting of:
cyclohexylalanyl;
leucyl; and
N-methylleucyl; and $R^2$ is of the formula —$NR^4R^5$; wherein
$R^4$ is selected from the group consisting of:
hydrogen;
methyl; and
ethyl;

$R^5$ is selected from the group consisting of:
lower alkyl; and
lower alkyl-$R^6$; and $R^6$ is selected from the group consisting of amino, guanidino, hydrogen, hydroxy, phenyl, morpholinyl, piperidinyl, pyrrolyl, pyridyl, pyrrolidinyl, pyrrolidinonyl, and quinuclidinyl; and wherein the piperidinyl, pyrrolyl, pyrrolidinyl, and pyrrolidinonyl groups are optionally substituted with a methyl group.

Another aspect of the invention relates to pharmaceutical formulations comprising the compounds of the invention or pharmaceutically acceptable salts, esters, or prodrugs thereof.

In another aspect, the invention relates to a method of modulating gonadotropin hormones in a mammal comprising administering to a mammal in need of such treatment a therapeutically effective amount of a compound as defined above.

Yet another aspect of the invention relates to a process for preparing compounds of the invention or pharmaceutically acceptable salts, esters, or prodrugs thereof.

DETAILED DESCRIPTION OF THE INVENTION

The invention relates to novel LHRH analogs of seven amino acyl residues represented by the formula (I), wherein A, B, C, D, E, F, and G represent amino acyl residues as described above. A lower alkyl group of one to ten carbons, represented by $R^1$, attaches via a carbonyl moiety to the N-terminal nitrogen atom of the representative amino acyl residue A. An N-alkylated nitrogen atom forms an amide bond with the C-terminal carbon atom of the representative amino acyl residue G.

Compounds of the invention provide LHRH analogs wherein the 10 to 8 amino acids from the C-terminus carboxylic acid moiety of a decapeptide LHRH antagonist sequence is eliminated. The compounds exhibit effective LHRH antagonist activity and are useful in treating disorders related to high levels of reproductive hormones. The lower molecular weight of the present compounds allows for improved oral bioavailability in administering treatment for various hormone-dependent diseases.

As used herein, the term "lower alkyl" refers to straight or branched chain alkyl radicals containing from 1 to 10 carbon atoms including, but not limited to methyl, ethyl, n-propyl, isopropyl (Isp), n-butyl (nBu), isobutyl, sec-butyl, t-butyl, diethyl, and the like.

Unless otherwise indicated by the "D" prefix, the stereochemistry of the alpha-carbon atom of the amino acids and aminoacyl residues in peptides described in this specification and the appended claims is the natural or "L" configuration.

As set forth above, the conventional abbreviations for the various common amino acids are used as generally accepted in the art and as recommended by the IUPAC-IUB Commission on Biochemical Nomenclature, *Biochemistry II*, 1726 (1972). These represent L-aminoacids, with the exception of the achiral amino acid glycine, and with the further exception of any unnatural or natural amino acids which are achiral, or otherwise designated as D-. All peptide sequences mentioned herein are written accordingly to the generally accepted convention whereby the N-terminal amino acid is on the left and the C-terminal amino acid is on the right. Further information on the nomenclature of peptides is described in *Pure Appl. Chem.*, 56:595 (1984).

Other abbreviations which are useful in describing the invention are the following:

| Amino acids, protecting groups, reagents | Abbreviation |
|---|---|
| 3-(1-naphthyl)-D-alanyl | D1Nal |
| 3-(2-naphthyl)-D-alanyl | D2Nal |
| 3-(3-pyridyl)-D-alanyl | D3Pal |
| N-acetyl-[3-(2-naphthyl)-D-alanyl] | NAcD2Nal |
| Arginyl | Arg |
| D-arginyl | DArg |
| D-asparaginyl | DAsn |
| D-citrullyl | DCit |
| Cyclohexylalanyl | Cha |
| D-glutamyl | DGln |
| D-2-amino-6-$N^G,N^G$-diethylguanidinohexanoyl | DHarg($Et_2$) |
| D-homocitrullyl | DHcit |
| (N-epsilon-nicotinyl)lysyl | Lys(Nic) |
| (N-epsilon-nicotinyl)-D-lysyl | DLys(Nic) |
| N-methyltyrosyl | NMeTyr |
| Leucyl | Leu |
| N-methylleucyl | NMeLeu |
| Phenylalanyl | Phe |
| [4-(N-acetyl)]-phenylalanyl | Phe(4-NAc) |
| [3-(4-chloro)]-D-phenylalanyl | D4ClPhe |
| N-methylphenylalanyl | NMePhe |
| [4-(N-acetyl)]-N-methylphenylalanyl | NMePhe(4-NAc) |
| [4-(N-nitro)]-N-methylphenylalanyl | NMePhe(4-$NO_2$) |
| [4-(3-amino-1,2,4-triazol-5-yl)]-N-methylphenylalanyl | NMePhe(4-Atza) |
| [4-(N-acetyl)]-D-phenylalanyl | DPhe(4-NAc) |
| [4-(3-amino-1,2,4-triazol-5-yl)]phenylalanyl | Phe(Atza) |
| [4-(3-amino-1,2,4-triazol-5-yl)]-D-phenylalanyl | DPhe(4-Atza) |
| Sarcosyl | Sar |
| Seryl | Ser |
| 1,2,3,4-tetrahydroisoquinoline-3-carbonyl | Tic |
| D-tryptyl | DTrp |
| Tyrosyl | Tyr |

The compounds of the present invention are useful in modulating levels of gonadotropin and androgen secretion in mammals. The compounds are particularly useful for their activity as LHRH antagonists or agonists.

The term "pharmaceutically acceptable salt" as used herein refers to acid addition salts of the compounds of formula (I) which are, within the scope of sound medical judgement, suitable for use in contact with the tissues of mammals, including humans and lower animals, without undue toxicity, irritation, allergic response, and the like commensurate with a reasonable benefit/risk ratio, and which are effective for their intended use. Pharmaceutically acceptable salts are well known in the art, and are summarized in S. M. Berge, et al., *J. Pharmaceutical Sciences* 66:1–19 (1977). The salts can be prepared in situt during the final isolation and purification of the compounds of the invention, or separately by reacting the free base function with a suitable organic acid. Examples of pharmaceutically acceptable, nontoxic acid addition salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalene-sulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, loweralkylsulfonate and aryl sulfonate.

The term "pharmaceutically acceptable ester" as used herein refers to non-toxic esters of the compounds of formula (I) derived by the condensation of a compound of the invention with an alcohol. Examples of pharmaceutically acceptable, non-toxic esters of the compounds of the invention include $C_1$ to $C_6$ alkanoyl esters wherein the alkanoyl group is a straight or branched chain, such as formate, acetate, propanoate, butyrate, isopropanoate, pentanoate, hexanoate, and the like. Esters of the compounds of the present invention may be prepared according to conventional methods.

The term "pharmaceutically acceptable prodrug" as used herein refers to biolabile compounds or derivatives which, upon delivery or administration to a treatment subject, are converted to in vivo parent compounds of the formula (I) above. Prodrugs of compounds of the invention are suitable for use in contact with the tissues of mammals, including humans and lower animals, without undue toxicity, irritation, allergic response, and the like commensurate with a reasonable benefit/risk ratio as determined by one of ordinary skill in the medical arts within the scope of sound medical judgement, and which are effective for their intended use, as well as the zwitterionic forms, where possible, of the compounds of the invention. Prodrugs are well-known in the art, and generally refers to compounds that are rapidly transformed in vivo to yield the parent compound of formula (I), for example by hydrolysis in blood. A summary of the art is described in T. Higuchi and V. Stella, "Pro-drugs as Novel Delivery Systems," Vol. 14 of the A. C. S. Symposium Series and in *Bioreversible Carriers in Drug Design*, ed. Edward B. Roche, American Pharmaceutical Association and Pergamon Press, 1987. Such prodrugs are readily apparent to one of ordinary skill in the art and can be regarded as functional equivalents of the compounds of the invention.

Where appropriate, prodrugs of derivatives of compounds of the present invention may be prepared by any suitable method. For those compounds in which the prodrug moiety is an amino acid or peptide functionality, the condensation of the amino group with amino acids and peptides may effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method, and the like), the Woodward reagent K method, the DCC-HOBT (1-hydroxybenzotriazole) method and the like. Classical methods for amino acid condensation reactions are described in M. Bodansky, Y. S. Kausner and M. A. Ondetti, *Peptide Synthesis*, Second Edition, N.Y., 1976.

Representative of the invention are compounds of formula (I), or a pharmaceutically acceptable salt, ester or prodrug thereof, wherein $R^1$ is acetyl; A is 3-(2-naphthyl)-D-alanyl; B is [3-(4-chloro)]-D-phenylalanyl; C is 3-(3-pyridyl)-D-alanyl; D is seryl; E is N-methyltyrosyl; F is (N-epsilon-nicotinyl)-D-lysyl; G is leucyl; and $R^2$ is of the formula —$NR^4R^5$, wherein $R^4$ is hydrogen, and $R^5$ is selected from the group consisting of isopropyl, butyl, diethyl, and lower alkyl-$R^6$, wherein $R^6$ is selected from the group consisting of amino, guanidino, hydrogen, hydroxy, phenyl, morpholinyl, piperidinyl, methyl-piperidinyl, pyrrolyl, methylpyrrolyl, pyridyl, pyrrolidinyl, methylpyrrolidinyl, pyrrolidinonyl, and quinuclidinyl.

Other representative compounds of the invention are compounds of formula (I), or a pharmaceutically acceptable salt, ester or prodrug thereof, wherein $R^1$ is acetyl; A is 3-(2-naphthyl)-D-alanyl; B is [3-(4-chloro)]-D-phenylalanyl; C is 3-(3-pyridyl)-D-alanyl; D is seryl; E is an amino acyl residue selected from the group consisting of arginyl; (N-epsilon-nicotinyl)lysyl; N-methylphenylalanyl; [4-(3-amino-1,2,4-triazol-5-yl)]phenylalanyl; [4-(3-amino-1,2,4-triazol-5-yl)]-N-methylphenylalanyl; [4-(N-acetyl)]-N-methylphenylalanyl; [4-(N-nitro)]-N-methylphenylalanyl; [4-(N-acetyl)]-phenylalanyl; tyrosyl; and 1,2,3,4-tetrahydroisoquinoline-3-carbonyl; F is an amino acyl residue selected from the group consisting of D-arginyl; D-asparaginyl; D-citrullyl; D-glutamyl; D-homocitrullyl; D-2-amino-6-$N^GN^G$-diethylguanidinohexanoyl; [4-(3-amino-1,2,4-triazol-5-yl)]-D-phenylalanyl; [4-(N-acetyl)]-D-phenylalanyl; and D-tryptyl; G is leucyl; and $R^2$ is of the formula —$NR^4R^5$, wherein $R^4$ is hydrogen, and $R^5$ is selected from the group consisting of isopropyl, butyl, diethyl, and lower alkyl-$R^6$, wherein $R^6$ is selected from the group consisting of amino, guanidino, hydrogen, hydroxy, phenyl, morpholinyl, piperidinyl, methylpiperidinyl, pyrrolyl, methylpyrrolyl, pyridyl, pyrrolidinyl, methylpyrrolidinyl, pyrrolidinonyl, and quinuclidinyl.

Yet other representative compounds of the invention are compound of formula (I), or a pharmaceutically acceptable salt, ester or prodrug thereof, wherein $R^1$ is acetyl; A is 3-(2-naphthyl)-D-alanyl; B is [3-(4-chloro)]-D-phenylalanyl; C is 3-(3-pyridyl)-D-alanyl; D is seryl; E is an amino acyl residue selected from the group consisting of arginyl; (N-epsilon-nicotinyl)lysyl;

N-metihylpheniylalanyl; [4-(3-amino-1,2,4-triazol-5-yl)]phenylalanyl; [4-(3-amino-1,2,4-triazol-5-yl)]-N-methylphenylalanyl; [4-(N-acetyl)]-N-methylphenylalanyl; [4-(N-nitro)]-N-methylphenylalanyl; [4-(N-acetyl)]-phenylalanyl; tyrosyl; and 1,2,3,4-tetrahydroisoquinoline-3-carbonyl; F is an amino acyl residue selected from the group consisting of D-arginyl: D-asparaginyl; D-citrullyl; D-glutamyl; D-homocitrullyl; D-2-amino-6-$N^G,N^G$-diethylcuanidinohexanoyl; [4-(3-amino-1,2,4-triazol-5-yl)]-D-phenylalanyl; [4-(N-acetyl)]-D-phenylalanyl; and D-tryptyl; G is leucyl; and $R^2$ is a group of the formula —NH—$(CH_2)_2$-(1-pyrrolidine).

Representative examples of compounds contemplated as within the scope of the present invention include, but are not limited to the following:

NAcD2Nal-D4ClPhe-D3Pal-Ser-NMeTyr-DLys(Nic)-Leu-NH-nBu;
NAcD2Nal-D4ClPhe-D3Pal-Ser-NMeTyr-DLys(Nic)-Leu-NH—$(CH_2)_2NH_2$;
NAcD2Nal-D4ClPhe-D3Pal-Ser-NMeTyr-DLys(Nic)-Leu-NH—$(CH_2)_2$-(1-pyrrolidine);
NAcD2Nal-D4ClPhe-D3Pal-Ser-NMeTyr-DLys(Nic)-Leu-N$(CH_2CH_3)_2$;
NAcD2Nal-D4ClPhe-D3Pal-Ser-NMeTyr-DLys(Nic)-Leu-NH—$(CH_2)_6NH_2$;
NAcD2Nal-D4ClPhe-D3Pal-Ser-NMeTyr-DLys(Nic)-Leu-NH—$(CH_2)_4NH_2$;
NAcD2Nal-D4ClPhe-D3Pal-Ser-NMeTyr-DLys(Nic)-Leu-NH—$(CH_2)_2OH$;
NAcD2Nal-D4ClPhe-D3Pal-Ser-NMeTyr-DLys(Nic)-Leu-NH—$(CH_2)_2$-phenyl;
NAcD2Nal-D4ClPhe-D3Pal-Ser-NMeTyr-DLys(Nic)-Leu-NH—$(CH_2)_2$NH-isopropyl;
NAcD2Nal-D4ClPhe-D3Pal-Ser-NMeTyr-DLys(Nic)-Leu-NH—$(CH_2)_7NH_2$;
NAcD2Nal-D4ClPhe-D3Pal-Ser-NMeTyr-DLys(Nic)-Leu-NH—$(CH_2)_6$NH(C=NH)$NH_2$;
NAcD2Nal-D4ClPhe-D3Pal-Ser-NMeTyr-DLys(Nic)-Leu-NH—$(CH_2)_5$NH-isopropyl;
NAcD2Nal-D4ClPhe-D3Pal-Ser-NMeTyr-DLys(Nic)-Leu-NH—$(CH_2)_5NH_2$;
NAcD2Nal-D4ClPhe-D3Pal-Ser-NMeTyr-DLys(Nic)-Leu-NH—$(CH_2)_5$NH(C=NH)$NH_2$;
NAcD2Nal-D4ClPhe-D3Pal-Ser-NMeTyr-DLys(Nic)-Leu-NH—$(CH_2)_3NH_2$;
NAcD2Nal-D4ClPhe-D3Pal-Ser-NMeTyr-DLys(Nic)-Leu-NH—$(CH_2)_2$NH(C=NH)$NH_2$;
NAcD2Nal-D4ClPhe-D3Pal-Ser-NMeTyr-DLys(Nic)-Leu-NH—$(CH_2)_{10}NH_2$;
NAcD2Nal-D4ClPhe-D3Pal-Ser-NMeTyr-DLys(Nic)-Leu-NH—$(CH_2)_8NH_2$;
NAcD2Nal-D4ClPhe-D3Pal-Ser-NMeTyr-DLys(Nic)-Leu-NH—$(CH_2)_2NHCH_3$;
NAcD2Nal-D4ClPhe-D3Pal-Ser-NMeTyr-DLys(Nic)-Leu-NH—$(CH_2)_8$NH(C=NH)$NH_2$;
NAcD2Nal-D4ClPhe-D3Pal-Ser-NMeTyr-DLys(Nic)-Leu-NH—$(CH_2)_{10}$NH-isopropyl;
NAcD2Nal-D4ClPhe-D3Pal-Ser-NMeTyr-DLys(Nic)-Leu-NH—$(CH_2)_4$NH(C=NH)$NH_2$;
NAcD2Nal-D4ClPhe-D3Pal-Ser-NMeTyr-DLys(Nic)-Leu-NH—$(CH_2)_4$NH(C=NH)$NH_2$;
NAcD2Nal-D4ClPhe-D3Pal-Ser-NMeTyr-DLys(Nic)-Leu-NH—$CH_2$-(2-pyridine);
NAcD2Nal-D4ClPhe-D3Pal-Ser-NMeTyr-DLys(Nic)-Leu-NH—$CH_2$-(3-pyridine);
NAcD2Nal-D4ClPhe-D3Pal-Ser-NMeTyr-DLys(Nic)-Leu-NH—(3-quinuclidine);
NAcD2Nal-D4ClPhe-D3Pal-Ser-NMeTyr-DLys(Nic)-Leu-NH—$CH_2CH_2$-(1-piperidine);
NAcD2Nal-D4ClPhe-D3Pal-Ser-NMeTyr-DLys(Nic)-Leu-NH—$CH_2CH_2$-(1-morpholine);
NAcD2Nal-D4ClPhe-D3Pal-Ser-NMeTyr-DLys(Nic)-Leu-NH—$CH_2CH_2$-(2-pyridine);
NAcD2Nal-D4ClPhe-D3Pal-Ser-NMeTyr-DLys(Nic)-Leu-NH—$CH_2CH_2$-[2-(1-methyl)pyrrole];
NAcD2Nal-D4ClPhe-D3Pal-Ser-NMeTyr-DLys(Nic)-Leu-NH—$CH_2CH_2$-[2-(1-methyl)pyrrolidine];
NAcD2Nal-D4ClPhe-D3Pal-Ser-NMeTyr-DLys(Nic)-Leu-NH—$CH_2CH_2CH_2$-(1-morpholine);
NAcD2Nal-D4ClPhe-D3Pal-Ser-NMeTyr-DLys(Nic)-Leu-NH—$CH_2CH_2CH_2$—N[(2-methyl)piperidine];
NAcD2Nal-D4ClPhe-D3Pal-Ser-NMeTyr-DLys(Nic)-Leu-NH—$CH_2CH_2CH_2$-(1-pyrrolidin-2-one);
NAcD2Nal-D4ClPhe-D3Pal-Ser-NMeTyr-DLys(Nic)-Leu-NH—$CH_2CH_2$—$CH_2CH_2OH$;
NAcD2Nal-D4ClPhe-D3Pal-Ser-NMeTyr-DLys(Nic)-Leu-NH$(CH_2)_9NH_2$;
NAcD2Nal-D4ClPhe-D3Pal-Ser-Tyr-DLys(Nic)-Leu-NH—$(CH_2)_2$-(1-pyrrolidine);
NAcD2Nal-D4ClPhe-D3Pal-Ser-Tyr-DCit-Leu-NH—$(CH_2)_2$-(1-pyrrolidine);
NAcD2Nal-D4ClPhe-D3Pal-Ser-Tyr-DCit-Leu-NH—$(CH_2)_2$-(1-pyrrolidine);
NAcD2Nal-D4ClPhe-D3Pal-Ser-NMeTyr-DCit-Leu-NH—$(CH_2)_2$-(1-pyrrolidine);
NAcD2Nal-D4ClPhe-D3Pal-Ser-DLys(Nic)-DLys(Nic)-Leu-NH—$(CH_2)_2$-(1-pyrrolidine);
NAcD2Nal-D4ClPhe-D3Pal-Ser-Arg-DTrp-Leu-NH—$(CH_2)_2$-(1-pyrrolidine);
NAcD2Nal-D4ClPhe-D3Pal-Ser-Tic-DLys(Nic)-Leu-NH—$(CH_2)_2$-(1-pyrrolidine);
NAcD2Nal-D4ClPhe-D3Pal-Ser-NMePhe-DLys(Nic)-Leu-NH—$(CH_2)_2$-(1-pyrrolidine);
NAcSar-D4ClPhe-D1Nal-Ser-NMeTyr-DLys(Nic)-Leu-NH—$(CH_2)_2$-(1-pyrrolidine);
NAcD2Nal-D4ClPhe-D3Pal-Ser-NMeTyr-DArg-Leu-NH—$(CH_2)_2$-(1-pyrrolidine);
NAcD2Nal-D4ClPhe-D3Pal-Ser-NMePhe(4-NAc)-DPhe(4-NAc)-Leu-NH—$(CH_2)_2$-(1-pyrrolidine);
NAcD2Nal-D4ClPhe-D3Pal-Ser-NMePhe(4-$NO_2$)-DCit-Leu-NH—$(CH_2)_2$-(1-pyrrolidine);
NAcD2Nal-D4ClPhe-D3Pal-Ser-Phe(4-Atza)-DPhe(4-Atza)-Leu-NH—$(CH_2)_2$-(1-pyrrolidine);
NAcD2Nal-D4ClPhe-D3Pal-Ser-NMePhe(4-Atza)-DPhe(4-Atza)-Leu-NH—$(CH_2)_2$-(1-pyrrolidine); and
NAcD2Nal-D4ClPhe-D3Pal-Ser-Phe(4-NAc)-DPhe(4-NAc)-Leu-NH—$(CH_2)_2$-(1-pyrrolidine).

Another aspect of the present invention relates to pharmaceutical compositions comprising a compound of the present invention as the active ingredient and a pharmaceutically acceptable carrier. Pharmaceutically acceptable carriers suitable for the pharmaceutical compositions of the invention comprise non-toxic compatible substances useful for preparing a composition for administering the compound to a mammal in need of treatment.

Suitable pharmaceutically acceptable carriers generally include, but are not limited to, non-toxic, inert solid, semi-solid, or liquid filler, diluent, encapsulating material or formulation auxiliary of any type. Exemplary material which can serve as pharmaceutically acceptable carriers are sugars, such as lactose, glucose, and sucrose; starches, such as corn starch and potato starch; cellulose and its derivatives, such as sodium carboxymethylcellulose, ethylcellulose and cellulose acetate; powdered tragacanth; malt; gelatin; talc, excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol, and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the pharmaceutically acceptable composition.

In another aspect of the invention, the invention relates to a method of modulating gonadotropic hormones in a mammal comprising administering to a mammal in need of such treatment a therapeutically effective amount of a compound as defined above. Condition for which an amount of the compound may be effective can be described as excessive tissue swelling, precocious puberty, hormonal imbalance, and other related conditions. Exemplary known symptoms and conditions for which the compounds are useful in treating include, but are not limited to, benign prostate hypertrophy, dysmenorrhea, endometriosis, precocious puberty, prostate cancer, uterine fibroids, prostate necrosis, and other sex hormone dependent diseases. These compounds provide novel peptides for treatment regimens useful in treating such conditions.

Compounds of the invention are administered to a mammal in need of such treatment by any of a variety of routes depending on the specific end use. Generally, the means for administering the peptide to a mammal will be a method selected from treatments consisting of oral, parenteral, vaginal, rectal, buccal (including sublingual), transdermal, and intranasal administration. Parental routes of administration include, but are not limited to subcutaneously, intramuscularly, and intravenously. The exact method and route of administration can be determined by one of ordinary skill in the medical arts having knowledge and the ability to develop a reasoned judgment as to the form of treatment administered to the mammal in need of treatment.

The exact dose and regimen for administration may depend on a variety of any factors including, but not limited to, the need of the individual subject being treated, the type of treatment, the degree of affliction or need, and length and frequency of the treatment. Generally, dosage for the treatment is between about 0.01 and 10 milligram of the active ingredient per kilogram body weight per day. Preferably, in light of the general expediency of the treatment, the dose administered is from about 0.1 to about 5.0 mg/kg body weight per day. The administration may be accomplished in a single, daily administration or by distributing doses over several applications or by slow release in order to achieve the most effective results.

GENERAL PROCEDURE FOR PEPTIDE SYNTHESIS

Peptides of the present invention may be prepared by any techniques that are known to those skilled in the art. Commonly employed methods known in the art of peptide synthesis generally referred to as "solid phase" peptide synthesis, wherein sequential coupling of amino acids is accomplished attached to an inert solid support, and "solution phase" synthesis, the technique wherein amino acids are coupled in solution. Solid phase methods of synthesis on a support resin are described in J. M. Steward and J. D. Young, *Solid Phase Peptide Synthesis*, W. H. Freeman Co., San Francisco, 1963; and J. Meienhofer, *Hormonal Proteins and Peptides*, Vol. 2, p. 46, Academic Press (New York), 1973. Summary of classical solution phase synthesis techniques is recited in G. Schroder and K. Lupke, *The Peptides*, vol. 1, Academic Pressure (New York), 1965, and "The Practice of Peptide Synthesis" by M. Bodansky and Bodansky, A.

Starting materials used in these general methods of peptide synthesis comprise a suitable resin and one or more amino acids or derivatives thereof. Naturally occurring and commonly protected amino acids are commercially available or, alternatively, can be prepared with readily available starting materials by methods commonly known in the art.

The peptide is synthesized in solution by methods known to those with skill in the art. The methods are described in "The Practice of Peptide Synthesis" by M. Bodansky and Bodansky, A. Briefly, an amino acid is N-protected with a protecting group and is coupled to the next N-free amino acid with a suitable coupling reagent (described below) at 0° C. to ambient temperatures for about 1 to about 5 hours to afford a dipeptide fragment. The dipeptide fragment is deprotected to afford a free amine terminus and a subsequent protected amino acid is coupled to the fragment under the coupling conditions previously described.

Suitable protecting groups are selected from the group consisting of hydroxy protecting groups. Exemplary suitable protecting groups include, but are not limited to, t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5-dimethoxybenzyloxycarbonyl, o-nitrophenylsulfenyl, 2-cyano-t-butyloxycarbonyl-9-fluoroenylmethyloxycarbonyl (FMOC), and the like. The preferred protecting group is t-butyloxycarbonyl.

Coupling reagents suitable for the amino acid coupling are selected from the group consisting of N,N'-dicyclohexylcarbodiimide or N,N'-diisopropylcarbodiimide (DIC) with or without 1-hydroxybenzotriazole (HOBT), benzotriazol-1-yloxy-tris(dimethylamino)-phosphonium-hexafluorophosphate (BOP) and bis-(2-oxo-3-oxazolidinyl) phosphine chloride (BOPCl). The preferred reagent is N,N'-dicyclohexylcarbodiimide.

Deprotecting reagents suitable for removing the protecting groups are anhydrous liquid hydrogen fluoride in the presence of anisole and dimethylphosphite or other carbonium ion scavenger, hydrogen fluoride/pyridine complex, tris(tri-fluoroacetyl)boron and trifluoroacetic acid, hydrogen and palladium on carbon on polyvinylpyrrolidone, sodium in liquid ammonia. Preferably, the deprotecting agent is liquid hydrogen fluoride in the presence of anisole and dimethylphosphite.

In the solid phase synthesis, a solid support provides an inert surface to which an amino acid is attached. The solid support materials, typically resins, are inert to the reagents and reaction conditions of the peptide linkage formation as well as conditions for cleaving the final peptide from the solid support. Suitable solid supports useful for the above synthesis are chloromethylpolystyrene-divinylbenzene polymer, hydroxymethylpolystyrene-divinylbenzene polymer, benzyldrylaminopolystyrene-divinylbenzene polymer, and the like. Preferably, the support is chloromethyl-polystyrene-1% divinylbenzene polymer.

Typically, the amino acid is protected or derivatized before attaching the amino acid to the resin. As used in the description of the general procedures for the peptide synthesis, the term "amino acid" refers to amino acids, salts, esters and derivatives thereof suitable for sequencing in a peptide synthesis as determined by one of ordinary skill in the art. The amino acid residues are attached to the resin or a formed polypeptide chain as a salt to synthesis the polypeptide chain having the desired sequence and having the desired length. Suitable salts of the amino acid are cesium, tetramethylammonium, triethyl-ammonium, 1,5-diazabicyclo-[5.4.0]undec-5-ene salts, or the like. Preferably, the amino acid is coupled with the solid support as a cesium salt.

Protecting groups preferred for preparing the peptides provide stable moieties for protecting the alpha-amino function of the amino acids. The protecting groups used generally have properties of being stable to conditions of peptide linkage formation and can be readily removed without destruction of the growing peptide chain or racemization of any of the chiral centers contained therein. Suitable protecting groups are hydroxy protecting groups as described in the solution phase synthesis.

Coupling of the protected amino acid to the support is accomplished in an inert solvent. Solvents suitable for the coupling reaction include, but are not limited to, ethanol, dichloromethane, methylene chloride, acetonitrile. N,N-dimethyl-formamide (DMF), and the like, or a mixture thereof. Preferably, the solvent is ethanol or dimethylformamide. Typically, the reaction is carried out between about 40° C. and 60° C., from about 12 to about 48 hours. The preferred reaction is accomplished in DMF at about 50° C. for about 24 hours.

Coupling of subsequent protected amino acid residues and derivatives can be accomplished using an automatic peptide synthesizer. These synthesizers are well-known in the art. Coupling of the attached amino acid and residue with additional amino acids involves reacting the attached amino acid with a suitable coupling reagent for about 1 to 24 hours. Preferably, the reaction is carried out for 12 hours at a temperature of between 10° C. and 50° C. in the inert solvent. Each protected amino acid is introduced in 0.4 M concentration and approximately 3.5 molar excess. Preferably, the coupling reaction is carried out in a 1:1 mixture of dichloromethane and DMF at ambient temperatures. Suitable coupling agents are described in accordance with the preparation of compounds of the invention in solution phase.

Cleaving the polypeptide chain by aminolysis removes the final peptide chain from the solid support. Preferred cleaving reagents are alkylamines or fluoroalkylamines in the presence or absence of boron tribromide. The most preferred is 1-(2-aminoethyl)-pyrrolidine.

Deprotection is usually accomplished under anhydrous strong acidic conditions that remove the protecting groups without destroying the formed peptide chain or degrading the acid sensitive moieties present on the peptide chain. Preferred temperatures for carrying out the deprotection reaction are from about −10° C. to about +10° C. The most preferred reaction is carried out at 0° C. for about 30 minutes with a deprotecting agent as described in the solution phase synthesis.

Procedures of the invention can be better understood in accordance with the Examples. The Examples are meant to merely illustrate compounds and processes which can be carried out in accordance with invention are not meant to be limiting in any way.

EXAMPLES

Example 1

NAcD2Nal-D4ClPhe-D3Pal-Ser-NMeTyr-DLys (Nic)-Leu-NH-nBu

A solution of NAcD2Nal-D4ClPhe-D3Pal-Ser(OBzl)-NMeTyr(OBzl)-DLys(Nic)-Leu-OH (0.266 g) in THF (5 ml), synthesized by conventional solution peptide synthesis methods as described in "The Practice of Peptide Synthesis" by M. Bodansky and Bodansky, A., which is herein incorporated by reference, was treated at −20° C. with isobutyl-chloroformate (0.03 ml), triethylamine (0.075 ml) and n-butylamine (0.05 ml). The reaction mixture was stirred at room temperature for one hr, then poured into a saturated solution of sodium bicarbonate and stirred overnight. The solid precipitate was filtered, washed with water and dried in vacuo over $P_2O_5$. The dried solid was treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH-nBu, was obtained as trifluoroacetate salt: $R_t$=25.6 min; FAB Mass spec for $C_{67}H_{82}N_{11}O_{11}Cl$ m/z 1252 (M+1); Amino Acid Anal: 0.35 Ser; 1.06 NMeTyr; 1.00 Leu; 0.78 3Pal; 1.29 4ClPhe; 1.00 Lys.

Example 2

NAcD2Nal-D4ClPhe-D3Pal-Ser-NMeTyr-DLys (Nic)-Leu-NH—$(CH_2)_2NH_2$

A solution of NAcD2Nal-D4ClPhe-D3Pal-Ser(OBzl)-NMeTyr(OBzl)-DLys(Nic)-Leu-OBzl (0.2185 g) in THF (3 ml), synthesized by conventional solution peptide synthesis methods, as described in "The Practice of Peptide Synthesis" by M. Bodansky and Bodansky, A., was treated at room temperature with diaminoethane (0.05 ml). The reaction mixture was stirred for three days at room temperature, then diluted with ethyl acetate, washed with bicarbonate and brine solutions, dried and concentrated in vacuo. The residue was dried over $P_2O_5$ overnight and then was treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—$(CH_2)_2$ $NH_2$, was obtained as trifluoroacetate salt: $R_t$=19.5 min; FAB Mass spec for $C_{65}H_{79}N_{12}O_{11}Cl$ showed (M+1) @1239 m/z; Amino Acid Anal.: 0.36 Ser; 1.01 NMeTyr; 1.06 Leu; 0.77 3Pal; 1.23 4ClPhe; 1.00 Lys.

Example 3

NAcD2Nal-D4ClPhe-D3Pal-Ser-NMeTyr-DLys (Nic)-Leu-NH—$(CH_2)_2$-(1-pyrrolidine)

According to the procedure described in Example 1, a THF solution (3 ml) of NAcD2Nal-D4ClPhe-D3Pal-Ser (OBzl)-NMeTyr(OBzl)-DLys(Nic)-Leu-OH (0.234 g) was treated at −20 ° C. with isobutylchloroformate (0.03 ml), triethylamine (0.075 ml) and 1-(2-aminoethyl)pyrrolidine (0.03 ml). The reaction mixture was stirred at room temperature for ten days. The solvents and excess of reagents were removed in vacuo. The residue was dried in vacuo over $P_2O_5$ and then treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—$(CH_2)_2$-(1-pyrrolidine), was obtained as trifluoroacetate salt: $R_t$=21.2 min; FAB Mass spec for $C_{69}H_{85}N_{12}O_{11}Cl$ showed (M+H) @1293 m/z; Amino Acid Anal.: 0.36 Ser; 1.04 NMeTyr; 0.98 Leu; 0.78 3Pal; 1.25 4ClPhe; 1.02 Lys.

Example 4

NAcD2Nal-D4ClPhe-D3Pal-Ser-NMeTyr-DLys(Nic)-Leu-N($CH_2CH_3$)$_2$

According to the procedure described in Example 1, a THF (3.5 ml) solution of NAcD2Nal-D4ClPhe-D3Pal-Ser(OBzl)-NMeTyr(OBzl)-DLys(Nic)-Leu-OH (0.234 g) was treated at −20° C. with isobutylchloroformate (0.03 ml), triethylamine (0.075 ml) and diethylamine (0.03 ml). The reaction mixture was stirred at room temperature for ten days. The solvents and excess of reagents were removed in vacuo. The residue was dried in vacuo over $P_2O_5$ and then treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-N($CH_2CH_3$)$_2$, was obtained as trifluoroacetate salt: $R_t$=28.4 min; FAB Mass spec for $C_{67}H_{82}N_{11}O_{11}Cl$ showed (M+H) @1252 m/z; Amino Acid Anal.: 0.37 Ser; 1.04 NMeTyr; 0.99 Leu; 0.79 3Pal; 1.26 4ClPhe; 1.01 Lys.

Example 5

NAcD2Nal-D4ClPhe-D3Pal-Ser-NMeTyr-DLys(Nic)-Leu-NH—$(CH_2)_6NH_2$

According to the procedure described in Example 2, a DMF solution (3 ml) of NAcD2Nal-D4ClPhe-D3Pal-Ser(OBzl)-NMeTyr(OBzl)-DLys(Nic)-Leu-OBzl (0.2213 g) was treated at room temperature with 1,6-diaminohexane (0.5 ml). The reaction mixture was stirred overnight, then poured into water, the precipitate was filtered and dried over $P_2O_5$ overnight. The dry residue was treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and running a gradient, over 30 minutes, of 25–50% of acetonitrile/water containing 0. 1% trifluoroacetic acid. The desired product, NAcD2Nal-D4ClPhe-D3Pal-Ser-NMeTyr-DLys(Nic)-Leu-NH—$(CH_2)_6NH_2$, was obtained as trifluoroacetate salt: $R_t$=20.2 min; FAB Mass spec for $C_{69}H_{87}N_{12}O_{11}Cl$ showed (M+1) @1295 m/z; Amino Acid Anal.: 0.36 Ser; 1.06 NMeTyr; 1.00 Leu; 0.78 3Pal; 1.24 4ClPhe; 1.00 Lys.

Example 6

NAcD2Nal-D4ClPhe-D3Pal-Ser-NMeTyr-DLys(Nic)-Leu-NH—$(CH_2)_4NH_2$

The procedure described in Example 5 was used, but substituting 1,4-diamino-butane for 1,6-diaminohexane. After workup and drying of the product over $P_2O_5$ overnight, the residue was treated with anhydrous anisole (1 ml) and anhydrous HF (5 ml) at 0° C. for 1 hour. The excess of reagent was removed in vacuo. The residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—$(CH_2)_4NH_2$, was obtained as trifluoroacetate salt. $R_t$=19.4 min; FAB Mass spec for $C_{67}H_{83}N_{12}O_{11}Cl$ showed (M+1) @1267 m/z; Amino Acid Anal.: 0.36 Ser; 1.06 NMeTyr; 0.99 Leu; 0.78 3Pal; 1.25 4ClPhe; 1.01 Lys.

Example 7

NAcD2Nal-D4ClPhe-D3Pal-Ser-NMeTyr-DLys(Nic)-Leu-NH—$(CH_2)_2OH$

A solution of NAcD2Nal-D4ClPhe-D3Pal-Ser(OBzl)-NMeTyr(OBzl)-DLys(Nic)-Leu-OEt (0.2214 g) in DMF (1 ml), synthesized by conventional solution peptide synthesis methods as described in "The Practice of Peptide Synthesis" by M. Bodansky and Bodansky, A., was treated at room temperature with ethanolamine (1 ml). The reaction mixture was stirred at room temperature for seven days, then poured into a 10% $NaHCO_3$ solution and stirred for 5 min. The precipitate was filtered and then dried over $P_2O_5$ overnight and then was treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and running a gradient, over 30 minutes, of 25–50% of acetonitrile/water containing 0.1% trifluoroacetic acid. The desired product, NAcD2Nal-D4ClPhe-D3Pal-Ser-NMeTyr-DLys(Nic)-Leu-NH—$(CH_2)_2OH$, was obtained as trifluoroacetate salt: $R_t$=21.0 min; FAB Mass spec for $C_{65}H_{78}N_{11}O_{12}Cl$ showed (M+1) @1240 m/z; Amino Acid Anal.: 0.38 Ser; 1.00 NMeTyr; 1.02 Leu; 0.66 3Pal; 1.00 4ClPhe; 0.98 Lys.

Example 8

NAcD2Nal-D4ClPhe-D3Pal-Ser-NMeTyr-DLys(Nic)-Leu-NH—$(CH_2)_2$-phenyl

The procedure described in Example 7 was used, but substituting phenethylamine for ethanolamine. After workup and drying over $P_2O_5$ overnight, the dry residue was treated with anhydrous anisole (1 ml) and anhydrous HF (5 ml) at 0° C. for 1 hour. The excess of reagent was removed in vacuo. The residue was washed with ether and then purified by HPLC using C-18 reverse phase column and running a gradient of 25–50%, over 30 minutes, of acetonitrile/water containing 0.1% trifluoroacetic acid. The desired product, NAcD2Nal-D4ClPhe-D3Pal-Ser-NMeTyr-DLys(Nic)-Leu-NH—$(CH_2)_2$-phenyl, was obtained as trifluoroacetate salt: $R_t$=30.4 min; FAB Mass spec for $C_{71}H_{82}N_{11}O_{11}Cl$ showed (M+1) @1300 m/z; Amino Acid Anal.: 0.36 Ser; 1.06 NMeTyr; 0.99 Leu; 0.78 3Pal; 1.25 4ClPhe; 1.01 Lys.

Example 9

NAcD2Nal-D4ClPhe-D3Pal-Ser-NMeTyr-DLys(Nic)-Leu-NH—$(CH_2)_2$NH-isopropyl

NAcD2Nal-D4ClPhe-D3Pal-Ser(OBzl)-NMeTyr(OBzl)-DLys(Nic)-Leu-OBzl (0.2213 g) was treated at room temperature with 2-aminoethyl-N-isopropylamine (1.0 ml). The reaction mixture was stirred for two days, then was poured into 10% NaHCO$_3$ solution, the precipitate was filtered, dissolved in (1:1) acetonitrile/water and lyophilized. The dry residue was treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—(CH$_2$)$_2$NH-isopropyl, was obtained as trifluoroacetate salt: R$_t$=19.2 min; FAB Mass spec for C$_{68}$H$_{85}$N$_{12}$O$_{11}$Cl showed (M+1) @1281 m/z; Amino Acid Anal.: 0.39 Ser; 0.93 NMeTyr; 1.02 Leu; 0.65 3Pal; 0.99 4ClPhe; 0.98 Lys.

Example 10

NAcD2Nal-D4ClPhe-D3Pal-Ser-NMeTyr-DLys (Nic)-Leu-NH—(CH2)$_7$NH$_2$

The procedure described in Example 9 was used, but substituting 1,7-diamino-heptane for 2-aminoethyl-N-isopropylamine (1.0 ml). The reaction mixture was stirred for two days, then was poured into 10% NaHCO$_3$ solution, the precipitate was filtered, dissolved in (1:1) acetonitrile/water and lyophilized. The dry residue was treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—(CH$_2$)$_7$NH$_2$, was obtained as trifluoroacetate salt: R$_t$=21.0 min; FAB Mass spec for C$_{70}$H$_{89}$N$_{12}$O$_{11}$Cl showed (M+1) @1309 m/z; Amino Acid Anal.: 0.38 Ser; 0.98 NMeTyr; 1.01 Leu; 0.66 3Pal; 1.00 4ClPhe; 0.99 Lys.

Example 11

NAcD2Nal-D4ClPhe-D3Pal-Ser-NMeTyr-DLys (Nic)-Leu-NH—(CH$_2$)$_6$NH(C=NH)NH$_2$

A solution of NAcD2Nal-D4ClPhe-D3Pal-Ser-NMeTyr-DLys(Nic)-Leu-NH—(CH$_2$)$_6$NH$_2$ (0.050 g) in DMF (1 ml) was treated with triethylamine (0.025 ml) and 3,5-dimethylpyrazole-1-carboxyamidine nitrate (0.050 g) at room temperature with stirring. The reaction mixture was stirred overnight and then concentrated in vacuo. The residue was poured into a 10% NaHCO$_3$ solution and stirred for 15 min. The precipitate was filtered and then dissolved in (1:1) acetonitrile/water and lyophilized. The dry residue was treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and rumning a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—(CH$_2$)$_6$-NH(C=NH)NH$_2$, was obtained as trifluoroacetate salt: R$_t$=21.6 min; FAB Mass spec for C$_{70}$H$_{89}$N$_{14}$O$_{11}$Cl showed (M+1) @1337 m/z; Amino Acid Anal.: 0.45 Ser; 1.05 NMeTyr; 1.01 Leu; 0.66 3Pal; 1.00 4ClPhe; 0.99 Lys.

Example 12

NAcD2Nal-D4ClPhe-D3Pal-Ser-NMeTyr-DLys (Nic)-1-Leu-NH—(CH$_2$)$_5$NH-isopropyl

A solution of NAcD2Nal-D4ClPhe-D3Pal-Ser-NMeTyr-DLys(Nic)-Leu-NH—(CH$_2$)$_4$NH$_2$ (0.074g) in ethanol (1 ml) was treated with sodium cyanoborohydride (0.0145 g) in the presence of acetone (2 ml). The reaction mixture was stirred at room temperature overnight, then was poured into a 10% solution of NaHCO$_3$ and stirred for 15 minutes. The precipitate was filtered, dissolved in (1:1) acetonitrile/water and lyophilized. The dry powder was treated with anhydrous anisole (1 ml) and anhydrous HF (5 ml) at 0° C. for 1 hour. The excess of reagent was removed in vacuo. The residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—(CH$_2$)$_5$NH-isopropyl, was obtained as trifluoroacetate salt: R$_t$=21.1 min; FAB Mass spec for C$_{71}$H$_{91}$N$_{12}$O$_{11}$Cl showed (M+1) @1323 m/z; Amino Acid Anal.: 0.44 Ser; 0.98 NMeTyr; 1.01 Leu; 0.66 3Pal; 1.01 4ClPhe; 0.99 Lys.

Example 13

NAcD2Nal-D4ClPhe-D3Pal-Ser-NMeTyr-DLys (Nic)-Leu-NH—(CH$_2$)$_5$NH$_2$

The procedure described in Example 7 was used, but substituting 1,5-diamino-pentane for ethanolamine. The reaction mixture was stirred at room temperature overnight, then was poured into a 10% solution of NaHCO$_3$ and stirred for 15 minutes. The precipitate was filtered, dissolved in (1:1) acetonitrile/water and lyophilized. The dry powder was treated with anhydrous anisole (1 ml) and anhydrous HF (5 ml) at 0° C. for 1 hour. The excess of reagent was removed in vacuo. The residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—(CH$_2$)$_5$NH$_2$, was obtained as trifluoroacetate salt: R$_t$=19.7 min; FAB Mass spec for C$_6$H$_{85}$N$_{12}$O$_{11}$Cl showed (M+1) @1281 m/z; Amino Acid Anal.: 0.44 Ser; 1.06 NMeTyr; 1.02 Leu; 0.65 3Pal; 1.11 4ClPhe; 0.97 Lys.

Example 14

NAcD2Nal-D4ClPhe-D3Pal-Ser-NMeTyr-DLys (Nic)-Leu-NH—(CH$_2$)$_5$NH(C=NH)NH$_2$

The procedure described in Example 11 was used, but substituting NAcD2Nal-D4ClPhe-D3Pal-Ser-NMeTyr-DLys(Nic)-Leu-NH—(CH$_2$)$_5$NH$_2$ for NAcD2Nal-D4ClPhe-D3Pal-Ser-NMeTyr-DLys(Nic)-Leu-NH—(CH$_2$)$_6$NH$_2$. The guanidino derivative was obtained, and purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—(CH$_2$)$_5$NH(C=NH)NH$_2$, was obtained as trifluoroacetate salt: R$_t$=20.8 min; FAB Mass spec for C$_{69}$H$_{87}$N$_{14}$O$_{11}$Cl showed (M+1) @1322 m/z; Amino Acid Anal.: 0.38 Ser; 0.98 NMeTyr; 1.01 Leu; 0.66 3Pal; 0.99 4ClPhe; 0.98 Lys.

Example 15

NAcD2Nal-D4ClPhe-D3Pal-Ser-NMeTyr-DLys (Nic)-Leu-NH—(CH$_2$)$_3$NH$_2$

The procedure described in Example 10 was used, but substituting 1,3-diamino-propane (1.0 ml) for 1,7-diaminoheptane. The reaction mixture was stirred for two days, then was poured into 10% NaHCO$_3$ solution. The precipitate was filtered, dissolved in (1:1) acetonitrile/water and lyophilized. The dry residue was treated with anhydrous anisole (1 ml) and anhydrous HF (5 ml) at 0° C. for 1 hour. The excess of reagent was removed in vacuo. The residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—$(CH_2)_3$NH$_2$, was obtained as trifluoroacetate salt: $R_t$=19.3 min; FAB Mass spec for $C_{66}H_{81}N_{12}O_{11}Cl$ showed (M+1) @1253 m/z; Amino Acid Anal.: 0.43 Ser; 1.04 NMeTyr; 1.02 Leu; 0.65 3Pal; 0.99 4ClPhe; 0.98 Lys.

Example 16
NAcD2Nal-D4ClPhe-D3Pal-Ser-NMeTyr-DLys(Nic)-Leu-NH—$(CH_2)_2$NH(C=NH)NH$_2$ Using the procedure described in Example 14, but substituting NAcD2Nal-D4ClPhe-D3Pal-Ser-NMeTyr-DLys(Nic)-Leu-NH—$(CH_2)_2$NH$_2$ for NAcD2Nal-D4ClPhe-D3Pal-Ser-NMeTyr-DLys(Nic)-Leu-NH—$(CH_2)_5$NH$_2$. The guanidino derivative was obtained, and purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—$(CH_2)_2$NH(C=NH)NH$_2$, was obtained as trifluoroacetate salt: $R_t$=19.5 min; FAB Mass spec for $C_{66}H_{81}N_{14}O_{11}Cl$ showed (M+1) @1281 m/z; Amino Acid Anal.: 0.42 Ser; 1.01 NMeTyr; 1.00 Leu; 0.67 3Pal; 1.01 4ClPhe; 1.00 Lys.

Example 17
NAcD2Nal-D4ClPhe-D3Pal-Ser-NMeTyr-DLys(Nic)-Leu-NH—$(CH_2)_{10}$NH$_2$ The procedure described in Example 10 was used, but substituting 1,10-diaminodecane (1.0 ml) for 1,7-diaminohexane. The reaction mixture was stirred for two days, then was poured into 10% NaHCO$_3$ solution, the precipitate was filtered, dissolved in (1:1) acetonitrile/water and lyophilized. The dry residue was treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—$(CH_2)_{10}$NH$_2$, was obtained as trifluoroacetate salt: $R_t$=24.4 min; FAB Mass spec for $C_{73}H_{95}N_{12}O_{11}Cl$ showed (M+1) @1351 m/z; Amino Acid Anal.: 0.40 Ser; 0.95 NMeTyr; 1.00 Leu; 0.66 3Pal; 1.01 4ClPhe; 0.99 Lys.

Example 18
NAcD2Nal-D4ClPhe-D3Pal-Ser-NMeTyr-DLys(Nic)-Leu-NH—$(CH_2)_8$NH$_2$ The procedure described in Example 10 was used, but substituting 1,8-diamino-octane (1.0 ml) for 1,10-diaminodecane. The reaction mixture was stirred for two days, then was poured into 10% NaHCO$_3$ solution. The precipitate was filtered, dissolved in (1:1) acetonitrile/water and lyophilized. The dry residue was treated with anhydrous anisole (1 ml) and anhydrous HF (5 ml) at 0° C. for 1 hour. The excess of reagent was removed in vacuo, the residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—$(CH_2)_8$NH$_2$, was obtained as trifluoroacetate: $R_t$=21.50 min; FAB Mass spec for $C_{71}H_{91}N_{12}O_{11}Cl$ showed (M+1) @1323 m/z; Amino Acid Anal.: 0.44 Ser; 1.05 NMeTyr; 1.01 Leu; 0.65 3Pal; 1.00 4ClPhe; 0.99 Lys.

Example 19
NAcD2Nal-D4ClPhe-D3Pal-Ser-NMeTyr-DLys(Nic)-Leu-NH—$(CH_2)_2$NHCH$_3$ The procedure described in Example 9, was used but substituting N-methyl-1,2-diaminoethane (0.5 g) for 2-aminoethyl-N-isopropylamine. The reaction mixture was stirred for two days, then was poured into 10% NaHCO$_3$ solution, the precipitate was filtered, dissolved in (1:1) acetonitrile/water and lyophilized. The dry residue was treated with anhydrous anisole (1 ml) and anhydrous HF (5 ml) at 0° C. for 1 hour. The excess of reagent was removed in vacuo. The residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—$(CH_2)_2$NH—CH$_3$, was obtained as trifluoroacetate salt: $R_t$=19.8 min; FAB Mass spec for $C_{66}H_{81}N_{12}O_{11}Cl$ showed (M+1) @1253 m/z; Amino Acid Anal.: 0.44 Ser; 1.03 NMeTyr; 1.01 Leu; 0.66 3Pal; 1.00 4ClPhe; 0.99 Lys.

Example 20
NAcD2Nal-D4ClPhe-D3Pal-Ser-NMeTyr-DLys(Nic)-Leu-NH—$(CH_2)_8$NH(C=NH)NH$_2$ The procedure described in Example 16 was used, but substituting NAcD2Nal-D4ClPhe-D3Pal-Ser-NMeTyr-DLys(Nic)-Leu-NH—$(CH_2)_8$NH$_2$ for NAcD2Nal-D4ClPhe-D3Pal-Ser-NMeTyr-DLys(Nic)-Leu-NH—$(CH_2)_2$NH$_2$. The guanidino derivative was obtained, and purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—$(CH_2)_8$NH(C=NH)NH$_2$, was obtained as trifluoroacetate salt: $R_t$=23.8 min; FAB Mass spec for $C_{72}H_{93}N_{14}O_{11}Cl$ showed (M+1) @1365 m/z; Amino Acid Anal.: 0.47 Ser; 1.09 NMeTyr; 1.00 Leu; 1.06 3Pal; 1.07 4ClPhe; 1.00 Lys.

Example 21
NAcD2Nal-D4ClPhe-D3Pal-Ser-NMeTyr-DLys(Nic)-Leu-NH—$(CH_2)_{10}$NH-isopropyl An solution of NAcD2Nal-D4ClPhe-D3Pal-Ser-NMeTyr-DLys(Nic)-Leu-NH—$(CH_2)_{10}$NH$_2$ (0.074 g) in ethanol (1 ml) was treated with sodium cyanoborohydride (0.0159 g) in the presence of acetone (2 ml). The reaction mixture was stirred at room temperature overnight, then was poured into a 10% solution of NaHCO$_3$ and stirred for 15 minutes. The precipitate was filtered, dissolved in (1:1) acetonitrile/water and lyophilized. The dry powder was treated with anhydrous anisole (1 ml) and anhydrous HF (5 ml) at 0° C. for 1 hour. The excess of reagent wvas removed in vacuo. The residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—$(CH_2)_{10}$NH-isopropyl, was obtained as trifluoroacetate salt: $R_t$=27.3 min; FAB Mass spec for $C_{76}H_{102}N_{12}O_{11}Cl$ showed (M+1) @1394 m/z; Amino Acid Anal.: 0.48 Ser; 1.02 NMeTyr; 1.00 Leu; 1.06 3Pal; 1.07 4ClPhe; 1.00 Lys.

Example 22
NAcD2Nal-D4ClPhe-D3Pal-Ser-NMeTyr-DLys(Nic)-Leu-NH—$(CH_2)_4$NH(C=NH)NH$_2$ The procedure described in Example 14 was used, but substituting NAcD2Nal-D4ClPhe-D3Pal-Ser-NMeTyr- DLys(Nic)-Leu-NH—(CH$_2$)$_4$NH$_2$ for NAcD2Nal-D4ClPhe-D3Pal-Ser-NMeTyr-DLys(Nic)-Leu-NH—(CH$_2$)$_5$NH$_2$. The guanidino derivative was obtained. and purified by HPLC using C-18 reverse phase column and running a gradient, over 30 minutes, of 25–50% acetonitrile/water containing 0. 1% trifluoroacetic acid. The desired product, NAcD2Nal-D4ClPhe-D3Pal-Ser-NMeTyr-DLys(Nic)-Leu-NH—(CH$_2$)$_4$NH(C=NH)NH$_2$, was obtained as trifluoroacetate salt: R$_t$=20.5 min; FAB Mass spec for C$_{68}$H$_{85}$N$_{14}$O$_{11}$Cl showed (M+1) @1309 m/z; Amino Acid Anal.: 0.46 Ser; 1.02 NMeTyr; 1.00 Leu; 1.01 3Pal; 1.03 4ClPhe; 1.00 Lys.

Example 23

NAcD2Nal-D4ClPhe-D3Pal-Ser-NMeTyr-DLys(Nic)-Leu-NH—CH$_2$-(2-pyridine)

A solution of NAcD2Nal-D4ClPhe-D3Pal-Ser(OBzl)-NMeTyr(OBzl)-DLys(Nic)-Leu-OBzl (0.154 g) in DMF (1 ml) was treated at room temperature with 2-aminomethylpyridine (1.0 ml). The reaction mixture was stirred for five days, then was poured into 10% NaHCO$_3$ solution. The precipitate was filtered, dissolved in (1:1) acetonitrile/water and lyophilized. The dry residue was treated with anhydrous anisole (1 ml) and anhydrous HF (5 ml) at 0° C. for 1 hour. The excess of reagent was removed in vacuo. The residue was washed with ether and then purified by HPLC using C-18 reverse phase column and running a gradient, over 30 minutes, of 25–50% acetonitrile/water containing 0.1% trifluoroacetic acid. The desired product, NAcD2Nal-D4ClPhe-D3Pal-Ser-NMeTyr-DLys(Nic)-Leu-NH—CH$_2$-(2-pyridine), was obtained as trifluoroacetate salt: R$_t$=21.8 min; FAB Mass spec for C$_{69}$H$_{79}$N$_{12}$O$_{11}$Cl showed (M+1) @1287 m/z; Amino Acid Anal.: 0.42 Ser; 1.03 NMeTyr; 1.00 Leu; 1.00 3Pal; 1.04 4ClPhe; 1.00 Lys.

Example 24

NAcD2Nal-D4ClPhe-D3Pal-Ser-NMeTyr-DLys(Nic)-Leu-NH—CH$_2$-(3-pyridine)

The procedure described in Example 23 was used, but substituting 3-amino-methylpyridine for 2-aminomethylpyridine. After workup, cleaving of the protecting groups and HPLC purification, the desired product, NAcD2Nal-D4ClPhe-D3Pal-Ser-NMeTyr-DLys(Nic)-Leu-NH—CH$_2$-(3-pyridine), was obtained as trifluoroacetate salt: R$_t$=21.2 min; FAB Mass spec for C$_{69}$H$_{79}$N$_{12}$O$_{11}$Cl showed (M+1) @1287 m/z; Amino Acid Anal.: 0.38 Ser; 0.94 NMeTyr; 0.99 Leu; 1.00 3Pal; 1.04 4ClPhe; 1.00 Lys.

Example 25

NAcD2Nal-D4ClPhe-D3Pal-Ser-NMeTyr-Dlys(Nic)-Leu-NH—(3-guinuclidine)

A NAcD2Nal-D4ClPhc-D3Pal-Ser(OBzl)-NMeTyr(OBzl)-DLys(Nic)-Leu-OH (0.5171 g) in DMF (1 ml) was cooled to 0° C. and 3-aminoquinuclidine hydrochloride (0.0886 g) was added, followed by diisopropylethylamine (0.25 ml) and benzotriazol-1-yloxytris(dimethylamino-phosphonium)hexafluorophosphate (0.1771 g). The reaction mixture was stirred for 1 hr at low temperature and then overight at room temperature. The mixture was poured into 20% NaHCO$_3$ solution and stirred for 1 hour. The precipitate was filtered dissolved in methanol and the solution was concentrated in vacuo. The residue was dissolved in (1:1) acetonitrile/water and lyophilized. The dry powder was treated with anisole (1 ml) and then treated with anhydrous HF to remove the protecting groups as described in Example 1. HPLC purification of the crude material gave the desired product, NAcD2Nal-D4ClPhe-D3Pal-Ser-NMeTyr-DLys(Nic)-Leu-NH—(3-quinuclidine), which was obtained as trifluoroacetate salt: R$_t$=20.9 min; FAB Mass spec for C$_{70}$H$_{85}$N$_{12}$O$_{11}$Cl showed (M+1) @1304 m/z; Amino Acid Anal.: 0.37 Ser; 0.92 NMeTyr; 0.99 Leu; 0.93 3Pal; 1.08 4ClPhe; 1.00 Lys.

Example 26

NAcD2Nal-D4ClPhe-D3Pal-Ser-NMeTyr-DLys(Nic)-Leu-NH—CH$_2$—CH$_2$-(1-piperidine)

The procedure described in Example 23 was used, but substituting 2-aminoethyl-1-piperidine for 2-aminomethylpyridine. After work up, the cleaving of the protecting groups and HPLC purification, the desired product, NAcD2Nal-D4ClPhe-D3Pal-Ser-NMeTyr-DLys(Nic)-Leu-NH—CH$_2$—CH$_2$N-piperidine, was obtained as trifluoroacetate salt: R$_t$=22.5 min; FAB Mass spec for C$_{70}$H$_{87}$N$_{12}$O$_{11}$Cl showed (M+1) @1307 m/z; Amino Acid Anal.: 0.43 Ser; 1.03 NMeTyr; 1.01 Leu; 1.01 3Pal; 1.18 4ClPhe; 0.99 Lys.

Example 27

NAcD2Nal-D4ClPhe-D3Pal-Ser-NMeTyr-DLys(Nic)-Leu-NH—CH$_2$—CH$_2$-(1-norpholine)

The procedure described in Example 26 was used, but substituting 2-aminoethy-1-morpholine for 2-aminoethyl-1-piperidine. After work up, the cleaving of the protecting groups and HPLC purification, the desired product, NAcD2Nal-D4ClPhe-D3Pal-Ser-NMeTyr-DLys(Nic)-Leu-NH—CH$_2$—CH$_2$-(1-morpholine), was obtained as trifluoroacetate salt: R$_t$=20.9 min; FAB Mass spec for C$_{69}$H$_{85}$N$_{12}$O$_{12}$Cl showed (M+1) @1309 m/z; Amino Acid Anal.: 0.40 Ser; 0.89 NMeTyr; 0.99 Leu; 1.00 3Pal; 1.08 4ClPhe; 1.07 Lys.

Example 28

NAcD2Nal-D4ClPhe-D3Pal-Ser-NMeTyr-DLys(Nic)-Leu-NH—CH$_2$—CH$_2$-(2-pyridine)

The procedure described in Example 27 was used but substituting amino-ethylpyridine for aminoethylmorpholine. After work up, the cleaving of the protecting groups and HPLC purification, the desired product, NAcD2Nal-D4ClPhe-D3Pal-Ser-NMeTyr-DLys(Nic)-Leu-NH—CH$_2$—CH$_2$-(2-pyridine), was obtained as trifluoroacetate salt: R$_t$=22.2 min; FAB Mass spec for C$_{70}$H$_{81}$N$_{12}$O$_{11}$Cl showed (M+1) @1301 m/z; Amino Acid Anal.: 0.38 Ser; 1.07 NMeYyr; 0.99 Leu; 0.98 3Pal; 1.10 4ClPhe; 1.00 Lys.

Example 29

NAcD2Nal-D4ClPhe-D3Pal-Ser-NMeTyr-DLys(Nic)-Leu-NH—CH$_2$—CH$_2$-[2-(1-methyl)pyrrole]

The procedure described in Example 28 was used, but substituting 2-(2-aminoethyl)-1-methyl-pyrrole for amino-ethylpyridine. After work up, the cleaving of the protecting groups and HPLC purification, the desired product, NAcD2Nal-D4ClPhe-D3Pal-Ser-NMeTyr-DLys(Nic)-Leu-NH—CH$_2$—CH$_2$-[2-(1-methyl)pyrrole], was obtained as trifluoroacetatc salt: R$_t$=29.6 min; FAB Mass spec for C$_{70}$H$_{83}$N$_{12}$O$_{11}$Cl showed (M+1) @ 1303 m/z; Amino Acid Anal.: 0.44 Ser; 1.11 NMeTyr; 0.47 Leu; 1.06 3Pal; 1.22 4ClPhe; 1.00 Lys.

Example 30

NAcD2Nal-D4ClPhe-D3Pal-Ser-NMeTyr-DLys(Nic)-Leu-NH—CH$_2$—CH$_2$-[2-(1-methyl)pyrrolidine]

The procedure described in Example 29 was used, but substituting 2-(2-amino-ethyl)-1-methyl-pyrrolidine for 2-(2-aminoethyl)-1-methyl-pyrrole. After workup, the cleaving of the protecting groups and HPLC purification, the desired product, NAcD2Nal-D4ClPhe-D3Pal-Ser-NMeTyr-DLys(Nic)-Leu-NH—CH$_2$—CH$_2$-[2-(1-methyl)-pyrrolidine], was obtained as trifluoroacetate salt: R$_t$=21.5 min; FAB Mass spec for C$_{70}$H$_{87}$N$_{12}$O$_{11}$Cl showed (M+1) @ 1306 m/z; Amino Acid Anal.: 0.43 Ser; 1.08 NMeTyr; 1.01 Leu; 1.01 3Pal; 1.17 4ClPhe; 0.99 Lys.

Example 31

NAcD2Nal-D4ClPhe-D3Pal-Ser-NMeTyr-DLys(Nic)-Leu-NH—CH$_2$CH$_2$CH$_2$-(1-morpholine)

The procedure described in Example 27 was used, but substituting 4-(3-aminopropyl)morpholine for 2-aminoethylmorpholine. After work up, the cleaving of the protecting groups and HPLC purification, the desired product, NAcD2Nal-D4ClPhe-D3Pal-Ser-NMeTyr-DLys(Nic)-Leu-NH—CH$_2$CH$_2$CH$_2$-(1-morpholine), was obtained as trifluoroacetate salt: R$_t$=20.4 min; FAB Mass spec for C$_{70}$H$_{87}$N$_{12}$O$_{12}$Cl showed (M+1) @1323 m/z; Amino Acid Anal.: 0.43 Ser; 1.00 NMeTyr; 1.00 Leu; 1.02 3Pal; 1.18 4ClPhe; 1.00 Lys.

Example 32

NAcD2Nal-D4ClPhe-D3Pal-Ser-NMeTyr-DLys(Nic)-Leu-NH—CH$_2$CH$_2$CH$_2$-[1-(2-methyl)piperidine]

The procedure described in Example 31 was used, but substituting 2-methylpiperidine for 4-(3-aminopropyl)morpholine. After work up, the cleaving of the protecting groups and HPLC purification, the desired product, NAcD2Nal-D4ClPhe-D3Pal-Ser-NMeTyr-DLys(Nic)-Leu-NH—CH$_2$CH$_2$CH$_2$-[1-(2-methyl)piperidine], was obtained as trifluoroacetate salt: R$_t$=23.3 min; FAB Mass spec for C$_{72}$H$_{91}$N$_{12}$O$_{11}$Cl showed (M+1) @1335 m/z; Amino Acid Anal.: 0.41 Ser; 1.34 NMeTyr; 1.00 Leu; 1.09 3Pal; 1.05 4ClPhe; 1.00 Lys.

Example 33

NAcD2Nal-D4ClPhe-D3Pal-Ser-NMeTyr-DLys(Nic)-Leu-NH—CH$_2$CH$_2$CH$_2$-(1-pyrrolidin-2-one)

The procedure described in Example 31 was used, but substituting 1-(3-aminopropyl)pyrrolidin-2-one for aminopropylmorpholine. After work up, cleavage of protecting groups and HPLC purification, the desired product, NAcD2Nal-D4ClPhe-D3Pal-Ser-NMeTyr-DLys(Nic)-Leu-NH—CH$_2$CH$_2$CH$_2$-(1-pyrrolidin-2-one), was obtained as trifluoroacetate salt: R$_t$=25.7 min; FAB Mass spec for C$_{70}$H$_{85}$N$_{12}$O$_{11}$Cl showed (M+1) @1321 m/z; Amino Acid Anal.: 0.27 Ser; 0.98 NMeTyr; 1.00 Leu; 0.97 3Pal; 1.10 4ClPhe; 1.01 Lys.

Example 34

NAcD2Nal-D4ClPhe-D3Pal-Ser-NMeTyr-DLys(Nic)-Leu-NH—CH$_2$CH$_2$CH$_2$CH$_2$OH

The procedure described in Example 23 was used, but substituting 4-amino-butanol for 2-aminomethylpyridine. After work up, cleavage of protecting groups and HPLC purification, the desired product, NAcD2Nal-D4ClPhe-D3Pal-Ser-NMeTyr-DLys(Nic)-Leu-NH—CH$_2$CH$_2$CH$_2$CH$_2$OH, was obtained as trifluoroacetate salt: R$_t$=23.5 min; FAB Mass spec for C$_{67}$H$_{82}$N$_{11}$O$_{12}$Cl showed (M+1) @(1268 m/z; Amino Acid Anal.: 0.42 Ser; 1.36 NMeTyr; 1.00 Leu; 1.00 3Pal; 1.07 4ClPhe; 1.00 Lys.

Example 35

NAcD2Nal-D4ClPhe-D3Pal-Ser-NMeTyr-DLys(Nic)-Leu-NH(CH$_2$)$_9$NH$_2$

The procedure described in Example 34 was used, but substituting 1,9-diaminononane for 4-aminobutanol. After work up, cleavage of protecting groups and HPLC purification, the desired product, NAcD2Nal-D4ClPhe-D3Pal-Ser-NMeTyr-DLys(Nic)-Leu-NH(CH$_2$)$_9$NH$_2$, was obtained as trifluoroacetate salt: R$_t$=24.1 min; FAB Mass spec for C$_{72}$H$_{93}$N$_{12}$O$_{11}$Cl showed (M+1) @1337 m/z; Amino Acid Anal.: 0.45 Ser; 1.08 NMeTyr; 1.00 Leu; 1.01 3Pal; 1.17 4ClPhe; 1.00 Lys.

Example 36

NAcD2Nal-D4ClPhe-D3Pal-Ser-Tyr-DLys(Nic)-Leu-NH—(CH$_2$)$_2$-(1-pyrrolidine)

In the reaction vessel of a Milligen-Biosearch 9500 peptide synthesizer was placed 1 g (0.42 mmol) of BOC-Leu-0-resin (Merrifield resin). Subsequent amino acids were added sequentially according to the following synthetic cycle:

1. Deblocking, to remove the t-BOC oroup from the alpha-amino function of the peptide, was carried out using a solution of 45% trifluoroacetic acid (TFA), 2.5% anisole, 2.0% dimethyl phosphite, and 50.5% methylene chloride. The resin was prewashed with the deblocking solution for one minute and then the deblocking reaction was run for 20 minutes.
2. Base wash, to remove and neutralize the TFA used for deprotection, was carried out using a solution of 10% N,N'-diisopropylethylamine in methylene chloride. The resin was washed with base three times for one minute each time after a deblocking step.
3. Coupling reaction was carried out using a 3-fold molar excess of 0.3 M DMF solution of a t-BOC protected amino acid derivative along with a 3-fold molar excess of 0.3 M methylene chloride solution of diisopropyl-carbodiimide as activator. The activated amino acid was then coupled to the free alpha-amino grroup of the peptide-resin. The reaction time was as described in the synthesis protocol described below.
4. Wash, each reaction step was followed by three washes of one minute each: one of methylene chloride, one of (1:1) methylene chloride/DMF, and one of DMF.

Synthesis Protocol

The amino acids were coupled to the resin according the following order, number and duration of couplings:

| Order | Number-Duration |
|---|---|
| 1. BOC-Leu | two-1 h |
| 2. BOC-DLys(Nic) | two-1 h |
| 3. BOC-Tyr(O-2-Br-Cbz) | two-1 h |

-continued

| Order | Number-Duration |
|---|---|
| 4. BOC-Ser(OBzl) | two-1 h |
| 5. BOC-D3Pal | two-1 h |
| 6. BOC-D4ClPhe | two-1 h |
| 7. BOC-D2Nal | two-1 h |

Upon completion of the synthesis the peptide-resin was dried overnight over $P_2O_5$, under vacuum and then was treated at room temperature with anhydrous methylene chloride (10 ml) with stirring under $N_2$. To the slurry was added a 0.63 M solution of boron tribromide in methylene chloride (2 ml) and the mixture was stirred for one hr, then aminoethyl-N-pyrrolidine (0.3 ml) was added and stirring continued overnight. Methanol (1 ml) was added and the mixture was stirred for 15 min and filtered. The resin was washed thoroughly with methanol three times and the filtrate and washes were combined and concentrated in vacuo. The residue was dried in vacuo over $P_2O_5$ overnight and then treated with HF/anisole to remove protecting groups. After workup and lyophilization the crude product was purified by HPLC using C-18 reverse phase column and running a gradient of 25–50%, over 30 minutes, of acetonitrile/water containing 0.1% trifluoroacetic acid. The desired compound, NAcD2Nal-D4ClPhe-D3Pal-Ser-Tyr-DLys(Nic)-Leu-NH—$(CH_2)_2$-(1-pyrrolidine), was obtained as trifluoroacetate salt: $R_t$=20.6 min; FAB Mass spec for $C_{68}H_{83}N_{12}O_{11}$ Cl showed (M+H) @(1278 m/z; Amino Acid Anal.: 0.47 Ser; 0.91 Tyr; 1.03 Leu; 0.94 3Pal; 0.89 4ClPhe; 1.05 Lys.

Example 37

NAcD2Nal-D4ClPhe-D3Pal-Ser-Tyr-DCit-Leu-NH—$(CH_2)_2$-(1-pyrrolidine)

The procedure described in Example 36 was used, but substituting BOC-DCit for BOC-DLys(Nic). After workup and HPLC purification the desired product, NAcD2Nal-D4ClPhe-D3Pal-Ser-Tyr-DCit-Leu-NH—$(CH_2)_2$-(1-pyrrolidine), was obtained as trifluoroacetate salt: $R_t$=20.4 min; FAB Mass spec for $C_{62}H_{79}N_{12}O_{11}$Cl showed (M+1) @1203 m/z; Amino Acid Anal.: 0.51 Ser; 0.99 Tyr; 1.00 Leu; 1.02 3Pal; 1.01 4ClPhe; 1.01 Cit.

Example 38

NAcD2Nal-D4ClPhe-D3Pal-Ser-Tyr-DHcit-Leu-NH—$(CH_2)_2$-(1-pyrrolidine)

The procedure described in Example 37 was used, but substituting BOC-DHcit for BOC-Cit. After workup and HPLC purification the desired product, NAcD2Nal-D4ClPhe-D3Pal-Ser-Tyr-DHcit-Leu-NH—$(CH_2)_2$-(1-pyrrolidine), was obtained as trifluoroacetate salt: $R_t$=22.6 min; FAB Mass spec for $C_{63}H_{81}N_{12}O_{11}$Cl showed (M+H) @1217 m/z; Amino Acid Anal.: 0.41 Ser; 0.95 Tyr; 1.00 Leu; 0.95 3Pal; 1.31 4ClPhe.

Example 39

NAcD2Nal-D4ClPhe-D3Pal-Ser-NMeTyr-DCit-Leu-NH—$(CH_2)_2$-(1-pyrrolidine)

The procedure described in Example 36 is used, but substituting BOC-NMeTyr(OBzl) for BOC-Tyr(OBzl). After workup and HPLC purification the desired product, NAcD2Nal-D4ClPhe-D3Pal-Ser-NMeTyr-DCit-Leu-NH—$(CH_2)_2$-(1-pyrrolidine), is obtained as trifluoroacetate salt.

Example 40

NAcD2Nal-D4ClPhe-D3Pal-Ser-Lys(Nic)-DLys(Nic)-Leu-NH—$(CH_2)_2$-(1-pyrrolidine)

The procedure described in Example 36 is used, but substituting BOC-Lys(Nic) for BOC-Tyr(OBzl). After workup and HPLC purification the desired product, NAcD2Nal-D4ClPhe-D3Pal-Ser-Lys(Nic)-DLys(Nic)-Leu-NH—$(CH_2)_2$-(1-pyrrolidine), is obtained as trifluoroacetate salt.

Example 41

NAcD2Nal-D4ClPhe-D3Pal-Ser-Arg-DTrp-Leu-NH—$(CH_2)_2$-(1-pyrrolidine)

The procedure described in Example 36 is used, but substituting BOC-Arg(Ng-Tos) for BOC-Tyr(OBzl) and BOC-DTrp for BOC-DLys(Nic). After workup and HPLC purification the desired product, NAcD2Nal-D4ClPhe-D3Pal-Ser-Arg-DTrp-Leu-NH—$(CH_2)_2$-(1-pyrrolidine), is obtained as trifluoroacetate salt.

Example 42

NAcD2Nal-D4ClPhe-D3Pal-Ser-Tic-DLys(Nic)-Leu-NH—$(CH_2)_2$-(1-pyrrolidine)

The procedure described in Example 36 is used, but substituting BOC-Tic for BOC-Tyr(OBzl). After workup and HPLC purification the desired product, NAcD2Nal-D4ClPhe-D3Pal-Ser-Tic-DLys(Nic)-Leu-NH—$(CH_2)_2$-(1-pyrrolidine), is obtained as trifluoroacetate salt.

Example 43

NAcD2Nal-D4ClPhe-D3Pal-Ser-NMePhe-DLys(Nic)-Leu-NH—$(CH_2)_2$-(1-pyrrolidine)

The procedure described in Example 36 is used, but substituting BOC-NMePhe for BOC-Tyr(OBzl). After workup and HPLC purification the desired product, NAcD2Nal-D4ClPhe-D3Pal-Ser-NMePhe-DLys(Nic)-Leu-NH—$(CH_2)_2$-(1-pyrrolidine), is obtained as trifluoroacetate salt.

Example 44

NAcSar-D4ClPhe-D1Nal-Ser-NMeTyr-DLys(Nic)-Leu-NH—$(CH_2)_2$-(1-pyrrolidine)

The procedure described in Example 36 is used, but substituting BOC-Sar, BOC-D1Nal and BOC-NMeTyr(OBzl) for BOC-D2Nal, BOC-D3Pal and BOC-Tyr(OBzl), respectively. After workup and HPLC purification the desired product, NAcSar-D4ClPhe-D1Nal-Ser-NMeTyr-DLys(Nic)-Leu-NH—$(CH_2)_2$-(1-pyrrolidine), is obtained as trifluoroacetate salt.

Example 45

NAcD2Nal-D4ClPhe-D3Pal-Ser-NMeTyr-DArg-Leu-NH—$(CH_2)_2$-(1-pyrrolidine)

The procedure described in Example 36 is used, but substituting BOC-NMeTyr(OBz) and BOC-DArg(Tos) for BOC-Tyr(OBzl) and BOC-DLys(Nic), respectively. After workup and HPLC purification the desired product, NAcD2Nal-D4ClPhe-D3Pal-Ser-NMeTyr-DArg-Leu-NH—$(CH_2)_2$-(1-pyrrolidine), is obtained as trifluoroacetate salt.

Example 46

NAcD2Nal-D4ClPhe-D3Pal-Ser-NMePhe(4-NAc)-DPhe(4-NAc)-Leu-NH—(CH$_2$)$_2$-(1-Pyrrolidine)

The procedure described in Example 36 is used, but substituting BOC-NMePhe-(4-NAc) and BOC-DPhe(4-NAc) for BOC-Tyr(OBzl) and BOC-DLys(Nic) respectively. After workup and HPLC purification the desired product, NAcD2Nal-D4ClPhe-D3Pal-Ser-NMePhe(4-NAc)-DPhe(4-NAc)-Leu-NH—(CH$_2$)$_2$-(1-pyrrolidine), is obtained as trifluoroacetate salt.

Example 47

NAcD2Nal-D4ClPhe-D3Pal-Ser-NMePhe(4-NO$_2$)-DCit-Leu-NH—(CH$_2$)$_2$-(1-pyrrolidine)

The procedure described in Example 36 is used, but substituting BOC-NMePhe-(4-NO$_2$) and BOC-DCit for BOC-Tyr(OBzl) and BOC-DLys(Nic) respectively. After workup and HPLC purification the desired product, NAcD2Nal-D4ClPhe-D3Pal-Ser-NMePhe(4-NO$_2$)-DCit-Leu-NH—(CH$_2$)$_2$-(1-pyrrolidine), is obtained as trifluoroacetate salt.

Example 48

NAcD2Nal-D4ClPhe-D3Pal-Ser-NMePhe(4-Atza)-DPhe(4-Atza)-Leu-NH—(CH$_2$)$_2$-(1-pyrrolidine)

The procedure described in Example 36 was used, but substituting BOC-NMePhe(4-N-FMOC) and BOC-DPhe(4-N-FMOC) for BOC-Tyr(OBzl) and BOC-DLys(Nic), respectively. After the completion of the synthesis the peptide-resin is treated with 30% piperidine/DMF for 2 to 24 hr, to cleave the FMOC protecting group from the 4-amino group on the phenyl rings of the side chains. The peptide-resin is washed 3 times with methylene chloride, 3 times with DMF and reacted with 10- to 20-fold excess of diphenylcyanocarbodiimidate in DMF overnight, washed 3 times with methylene chloride, 3 times with DMF, and then reacted with 20- to 100-fold excess of hydrazine in DMF overnight. The peptide-resin is again washed, as previously described, dried over P$_2$O$_5$, overnight and then is treated at room temperature with anhydrous methylene chloride (10 ml) with stirring under N$_2$. To the slurry is added a 0.63 M solution of boron tribromide in methylene chloride (2 ml) and the mixture is stirred for one hour, then aminoethyl-N-pyrrolidine (0.3 ml) is added and stirring continued overnight. Methanol (1 ml) is added and the mixture was stirred for 15 min and filtered. The resin was washed thoroughly with methanol three times and the filtrate and the washes are combined and concentrated in vacuo. The residue is dried in vacuo over P$_2$O$_5$ overnight and then treated with HF/anisole to remove protecting groups. After workup and lyophilization the crude product is purified by HPLC to give the desired product NAcD2Nal-D4ClPhe-D3Pal-Ser-NMePhe(4-Atza)-DPhe(4-Atza)-Leu-NH—(CH$_2$)$_2$-(1-pyrrolidine) as the trifluoroacetate salt.

Example 49

NAcD2Nal-D4ClPhe-D3Pal-Ser-Phe(4-Atza)-DPhe(4-Atza)-Leu-NH—(CH$_2$)$_2$-(1-pyrrolidine)

The procedure described in Example 48 is used, but substituting BOC-Phe-(4-N-FMOC) for BOC-NMePhe(4-N-FMOC). After workup and lyophilization the crude product is purified by HPLC to give the desired product NAcD2Nal-D4ClPhe-D3Pal-Ser-Phe(4-Atza)-DPhe(4-Atza)-Leu-NH—(CH$_2$)$_2$-(1-pyrrolidine) as the tri fluoroacetate salt.

Example 50

NAcD2Nal-D4ClPhe-D3Pal-Ser-Phe(4-NAc)-DPhe(4-NAc)-Leu-NH—(CH$_2$)$_2$-(1-pyrrolidine)

The procedure described in Example 46 is used, but substituting BOC-Phe-(4-N-FMOC) for BOC-NMePhe(4-N-FMOC). After workup and lyophilization the crude product is purified by HPLC to give the desired product NAcD2Nal-D4ClPhe-D3Pat-Ser-Phe(4-NAc)-DPhe(4-NAc)-Leu-NH—(CH$_2$)$_2$-(1-pyrrolidine) as the trifluoroacetate salt.

LHRH ANTAGONIST ACTIVITY

Representative compounds of the present invention were evaluated in vitro for inhibition of LH release from rat pituitary cells (pA$_2$). Methods for the assay procedures arc described by F. Haviv, et al. *J. Med. Chem.*, 32:2340–2344 (1989). Values of pA$_2$ are the negative logarithms of the concentration of the particular antagonist test compound required to shift the response curve produced by the agonist leuprolide to two-fold higher concentration. Typically values of 7.0 or greater are indicative of good LHRH antagonist potency, with values of 8.0 or greater being preferred. Leuprolide LHRH agonist, disclosed and claimed in U.S. Pat. No. 4,005,063, has the structure 5-oxo-Pro$^1$-His$^2$-Trp$^3$-Ser$^4$-Tyr$^5$-D-Leu$^6$-Leu$^7$-Arg$^8$-Pro$^9$-NHEt.

Results for the assay of representative compounds in accordance with the invention are summarized in Table 1.

TABLE 1

| Example No. | LHRH Agonist Activity (pA$_2$) |
| --- | --- |
| 1 | 7.90 |
| 2 | 9.58 |
| 3 | 11.27 |
| 4 | 7.96 |
| 5 | 9.91 |
| 6 | 9.90 |
| 7 | 8.95 |
| 8 | 8.48 |
| 9 | 10.21 |
| 10 | 8.76 |
| 11 | 9.10 |
| 12 | 10.45 |
| 13 | 9.30 |
| 14 | 9.81 |
| 15 | 8.70 |
| 16 | 8.89 |
| 17 | 7.63 |
| 18 | 8.48 |
| 19 | 9.70 |
| 20 | 8.39 |
| 21 | 8.42 |
| 22 | 10.26 |
| 23 | 9.18 |
| 24 | 8.30 |
| 25 | 10.02 |
| 26 | 9.30 |
| 27 | 8.30 |
| 28 | 8.10 |
| 29 | 8.30 |
| 30 | 9.80 |
| 31 | 9.30 |
| 32 | 9.07 |
| 33 | 8.30 |
| 34 | 8.71 |

What is claimed is:

1. A peptide of the formula:

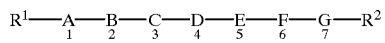 (I)

or a pharmaceutically acceptable salt or ester thereof, wherein:

$R^1$ is of the formula $R^3(C=O)—$, wherein $R^3$ is lower alkyl;

A is an amino acyl residue selected from the group consisting of:
   3-(2-naphthyl)-D-alanyl;
   [3-(4-chloro)]-D-phenylalanyl; and
   sarcosyl;

B is an amino acyl residue selected from the group consisting of:
   3-(1-naphthyl)-D-alanyl; and
   [3-(4-chloro)]-D-phenylalanyl;

C is an amino acyl residue selected from the group consisting of:
   3-(3-pyridyl)-D-alanyl; and
   3-(1-naphthyl)-D-alanyl;

D is seryl;

E is an acyl group selected from the group consisting of:
   arginyl;
   (N-epsilon-nicotinyl)lysyl;
   N-methylphenylalanyl;
   [4-(3-amino-1,2,4-triazol-5-yl)]phenylalanyl;
   [4-(3-amino-1,2,4-triazol-5-yl)]-N-methylphenylalanyl;
   [4-(N-acetyl)]-N-methylphenylalanyl;
   [4-(N-nitro)]-N-methylphenylalanyl;
   [4-(N-acetyl)]-phenylalanyl;
   tyrosyl;
   N-methyltyrosyl; and
   1,2,3,4-tetrahydroisoquinoline-3-carbonyl;

F is an amino acyl residue selected from the group consisting of:
   D-arginyl;
   D-asparaginyl;
   D-citrullyl;
   D-glutamyl;
   D-homocitrullyl;
   D-2-amino-6-$N^G$,$N^G$-diethylguanidinohexanoyl;
   (N-epsilon-nicotinyl)-D-lysyl;
   [4-(3-amino-1,2,4-triazol-5-yl)]-D-phenylalanyl;
   [4-(N-acetyl)]-D-phenylalanyl; and
   D-tryptyl;

G is an amino acyl residue selected from the group consisting of:
   cyclohexylalanyl;
   leucyl; and
   N-methylleucyl; and $R^2$ is of the formula $—NR^4R^5$; wherein $R^4$ is selected from the group consisting of:
   hydrogen;
   methyl; and
   ethyl;

$R^5$ is selected from the group consisting of:
   lower alkyl; and
   lower alkyl-$R^6$; and $R^6$ is selected from the group consisting of amino, guanidino, hydrogen, hydroxy, phenyl, morpholinyl, piperidinyl, pyrrolyl, pyridyl, pyrrolidinyl, pyrrolidinonyl and quinuclidinyl; and wherein the piperidinyl, pyrrolyl, pyrrolidinyl, and pyrrolidinonyl groups are optionally substituted with a methyl group.

2. A compound according to claim 1, or a pharmaceutically acceptable salt thereof, wherein:

$R^1$ is acetyl;
A is 3-(2-naphthyl)-D-alanyl;
B is [3-(4-chloro)]-D-phenylalanyl;
C is 3-(3-pyridyl)-D-alanyl;
D is seryl;
E is N-methyltyrosyl;
F is (N-epsilon-nicotinyl)-D-lysyl;
G is leucyl; and
$R^2$ is of the formula $—NR^4R^5$, wherein $R^4$ is hydrogen, and $R^5$ is selected from the group consisting of isopropyl, butyl, diethyl, and lower alkyl-$R^6$, wherein $R^6$ is selected from the group consisting of amino, guanidino, hydrogen, hydroxy, phenyl, morpholinyl, piperidinyl, methylpiperidinyl, pyrrolyl, methylpyrrolyl, pyridyl, pyrrolidinyl, methylpyrrolidiniyl, pyrrolidinonyl, and quinuclidinyl.

3. A compound according to claim 1, or a pharmaceutically acceptable salt ester thereof, wherein:

$R^1$ is acetyl;
A is 3-(2-naphthyl)-D-alanyl;
B is [3-(4-chloro)]-D-phenylalanyl;
C is 3-(3-pyridyl)-D-alanyl;
D is seryl;
E is an acyl group selected from the group consisting of:
   arginyl;
   (N-epsilon-nicotinyl)lysyl;
   N-methylphenylalanyl;
   [4-(3-amino-1,2,4-triazol-5-yl)]phenylalanyl;
   [4-(3-amino-1,2,4-triazol-5-yl)]-N-methylphenylalanyl;
   [4-(N-acetyl)]-N-methylphenylalanyl;
   [4-(N-nitro)]-N-methylphenylalanyl;
   [4-(N-acetyl)]-phenylalanyl;
   tyrosyl; and
   1,2,3,4-tetrahydroisoquinoline-3-carbonyl;

F is an amino acyl residue selected from the group consisting of:
   D-arginyl;
   D-asparaginyl;
   D-citrullyl;
   D-glutamyl;
   D-homocitrullyl;
   D-2-amino-6-$N^G$,$N^G$-diethylguanidinohexanoyl;
   [4-(3-amino-1,2,4-triazol-5-yl)]-D-phenylalanyl;
   [4-(N-acetyl)]-D-phenylalanyl; and
   D-tryptyl;

G is leucyl; and
$R^2$ is of the formula $—NR^4R^5$, wherein $R^4$ is hydrogen, and $R^5$ is selected from the group consisting of isopropyl, butyl, diethyl, and lower alkyl-$R^6$, wherein $R^6$ is selected from the group consisting of amino, guanidino, hydrogen, hydroxy, phenyl, morpholinyl, piperidinyl, methylpiperidinyl, pyrrolyl, methylpyrrolyl, pyridyl, pyrrolidinyl, methylpyrrolidinyl, pyrrolidinonyl, and quinuclidinyl.

4. A compound according to claim 3, or a pharmaceutically acceptable salt ester thereof, wherein $R^1$, A, B, C, D, E, F, and G are as defined in claim 3, and $R^2$ is a group of the formula $—NH—(CH_2)_2$-(1-pyrrolidine).

5. A pharmaceutical formulation comprising a pharmaceutically-acceptable carrier and compound according to claim 1, or a pharmaceutically acceptable salt or ester thereof.

6. A pharmaceutical formulation comprising a pharmaceutically-acceptable carrier and compound according to claim 2, or a pharmaceutically acceptable salt or ester thereof.

7. A pharmaceutical formulation comprising a pharmaceutically-acceptable carrier and compound according to claim 3, or a pharmaceutically acceptable salt ester thereof.

8. A pharmaceutical formulation comprising a pharmaceutically-acceptable carrier and compound according to claim 4, or a pharmaceutically acceptable salt ester thereof.

9. A method of modulating gonadotropin hormones in a mammal comprising administering to a mammal in need of the treatment a therapeutically effective amount of a compound according to claim 1.

10. A method of modulating gonadotropin hormones in a mammal comprising administering to a mammal in need of the treatment a therapeutically effective amount of a compound according to claim 2.

11. A method of modulating gonadotropin hormones in a mammal comprising administering to a mammal in need of the treatment a therapeutically effective amount of a compound according to claim 3.

12. A method of modulating gonadotropin hormones in a mammal comprising administering to a mammal in need of the treatment a therapeutically effective amount of a compound according to claim 4.

13. A compound according to claim 1, or a pharmaceutically acceptable salt or ester thereof, selected from the group consisting of:

NAcD2Nal-D4ClPhe-D3Pal-Ser-NMeTyr-DLys(Nic)-Leu-NH-nBu;

NAcD2Nal-D4ClPhe-D3Pal-Ser-NMeTyr-DLys(Nic)-Leu-NH—$(CH_2)_2NH_2$;

NAcD2Nal-D4ClPhe-D3Pal-Ser-NMeTyr-DLys(Nic)-Leu-NH—$(CH_2)_2$-(1-pyrrolidine);

NAcD2Nal-D4ClPhe-D3Pal-Ser-NMeTyr-DLys(Nic)-Leu-N$(CH_2CH_3)_2$;

NAcD2Nal-D4ClPhe-D3Pal-Ser-NMeTyr-DLys(Nic)-Leu-NH—$(CH_2)_6NH_2$;

NAcD2Nal-D4ClPhe-D3Pal-Ser-NMeTyr-DLys(Nic)-Leu-NH—$(CH_2)_4NH_2$;

NAcD2Nal-D4ClPhe-D3Pal-Ser-NMeTyr-DLys(Nic)-Leu-NH—$(CH_2)_2OH$;

NAcD2Nal-D4ClPhe-D3Pal-Ser-NMeTyr-DLys(Nic)-Leu-NH—$(CH_2)_2$-phenyl;

NAcD2Nal-D4ClPhe-D3Pal-Ser-NMeTyr-DLys(Nic)-Leu-NH—$(CH_2)_2$NH-isopropyl;

NAcD2Nal-D4ClPhe-D3Pal-Ser-NMeTyr-DLys(Nic)-Leu-NH—$(CH_2)_7NH_2$;

NAcD2Nal-D4ClPhe-D3Pal-Ser-NMeTyr-DLys(Nic)-Leu-NH—$(CH_2)_6$NH(C=NH)$NH_2$;

NAcD2Nal-D4ClPhe-D3Pal-Ser-NMeTyr-DLys(Nic)-Leu-NH—$(CH_2)_5$NH-isopropyl;

NAcD2Nal-D4ClPhe-D3Pal-Ser-NMeTyr-DLys(Nic)-Leu-NH—$(CH_2)_5NH_2$;

NAcD2Nal-D4ClPhe-D3Pal-Ser-NMeTyr-DLys(Nic)-Leu-NH—$(CH_2)_5$NH(C=NH)$NH_2$;

NAcD2Nal-D4ClPhe-D3Pal-Ser-NMeTyr-DLys(Nic)-Leu-NH—$(CH_2)_3NH_2$;

NAcD2Nal-D4ClPhe-D3Pal-Ser-NMeTyr-DLys(Nic)-Leu-NH—$(CH_2)_2$NH(C=NH)$NH_2$;

NAcD2Nal-D4ClPhe-D3Pal-Ser-NMeTyr-DLys(Nic)-Leu-NH—$(CH_2)_{10}NH_2$;

NAcD2Nal-D4ClPhe-D3Pal-Ser-NMeTyr-DLys(Nic)-Leu-NH—$(CH_2)_8NH_2$;

NAcD2Nal-D4ClPhe-D3Pal-Ser-NMeTyr-DLys(Nic)-Leu-NH—$(CH_2)_2NHCH_3$;

NAcD2Nal-D4ClPhe-D3Pal-Ser-NMeTyr-DLys(Nic)-Leu-NH—$(CH_2)_8$NH(C=NH)$NH_2$;

NAcD2Nal-D4ClPhe-D3Pal-Ser-NMeTyr-DLys(Nic)-Leu-NH—$(CH_2)_{10}$NH-isopropyl;

NAcD2Nal-D4ClPhe-D3Pal-Ser-NMeTyr-DLys(Nic)-Leu-NH—$(CH_2)_4$NH(C=NH)$NH_2$;

NAcD2Nal-D4ClPhe-D3Pal-Ser-NMeTyr-DLys(Nic)-Leu-NH—$(CH_2)_4$NH(C=NH)$NH_2$;

NAcD2Nal-D4ClPhe-D3Pal-Ser-NMeTyr-DLys(Nic)-Leu-NH—$CH_2$-(2-pyridine);

NAcD2Nal-D4ClPhe-D3Pal-Ser-NMeTyr-DLys(Nic)-Leu-NH—$CH_2$-(3-pyridine);

NAcD2Nal-D4ClPhe-D3Pal-Ser-NMeTyr-DLys(Nic)-Leu-NH—(3-quinuclidine);

NAcD2Nal-D4ClPhe-D3Pal-Ser-NMeTyr-DLys(Nic)-Leu-NH—$CH_2CH_2$-(1-piperidine);

NAcD2Nal-D4ClPhe-D3Pal-Ser-NMeTyr-DLys(Nic)-Leu-NH—$CH_2CH_2$-(1-morpholine);

NAcD2Nal-D4ClPhe-D3Pal-Ser-NMeTyr-DLys(Nic)-Leu-NH—$CH_2CH_2$-(2-pyridine);

NAcD2Nal-D4ClPhe-D3Pal-Ser-NMeTyr-DLys(Nic)-Leu-NH—$CH_2CH_2$-[2-(1-methyl)pyrrole];

NAcD2Nal-D4ClPhe-D3Pal-Ser-NMeTyr-DLys(Nic)-Leu-NH—$CH_2CH_2$-[2-(1-methyl)pyrrolidine];

NAcD2Nal-D4ClPhe-D3Pal-Ser-NMeTyr-DLys(Nic)-Leu-NH—$CH_2CH_2CH_2$-(1-morpholine);

NAcD2Nal-D4ClPhe-D3Pal-Ser-NMeTyr-DLys(Nic)-Leu-NH—$CH_2CH_2CH_2$-N[(2-methyl)piperidine];

NAcD2Nal-D4ClPhe-D3Pal-Ser-NMeTyr-DLys(Nic)-Leu-NH—$CH_2CH_2CH_2$(1-pyrrolidin-2-one);

NAcD2Nal-D4ClPhe-D3Pal-Ser-NMeTyr-DLys(Nic)-Leu-NH—$CH_2CH_2$—$CH_2CH_2OH$;

NAcD2Nal-D4ClPhe-D3Pal-Ser-NMeTyr-DLys(Nic)-Leu-NH$(CH_2)_9NH_2$;

NAcD2Nal-D4ClPhe-D3Pal-Ser-Tyr-DLys(Nic)-Leu-NH—$(CH_2)_2$-(1-pyrrolidine);

NAcD2Nal-D4ClPhe-D3Pal-Ser-Tyr-DCit-Leu-NH—$(CH_2)_2$-(1-pyrrolidine);

NAcD2Nal-D4ClPhe-D3Pal-Ser-Tyr-DHcit-Leu-NH—$(CH_2)_2$-(1-pyrrolidine);

NAcD2Nal-D4ClPhe-D3Pal-Ser-NMeTyr-DCit-Leu-NH—$(CH_2)_2$-(1-pyrrolidine);

NAcD2Nal-D4ClPhe-D3Pal-Ser-Lys(Nic)-DLys(Nic)-Leu-NH—$(CH_2)_2$-(1-pyrrolidine);

NAcD2Nal-D4ClPhe-D3Pal-Ser-Arg-DTrp-Leu-NH—$(CH_2)_2$-(1-pyrrolidine);

NAcD2Nal-D4ClPhe-D3Pal-Ser-Tic-DLys(Nic)-Leu-NH—$(CH_2)_2$-(1-pyrrolidine);

NAcD2Nal-D4ClPhe-D3Pal-Ser-NMePhe-DLys(Nic)-Leu-NH—$(CH_2)_2$-(1-pyrrolidine);

NAcSar-D4ClPhe-D1Nal-Ser-NMeTyr-DLys(Nic)-Leu-NH—$(CH_2)_2$-(1-pyrrolidine);

NAcD2Nal-D4ClPhe-D3Pal-Ser-NMeTyr-DArg-Leu-NH—$(CH_2)_2$-(1-pyrrolidine);

NAcD2Nal-D4ClPhe-D3Pal-Ser-NMePhe(4-NAc)-DPhe(4-NAc)-Leu-NH—(CH$_2$)$_2$-(1-pyrrolidine);

NAcD2Nal-D4ClPhe-D3Pal-Ser-NMePhe(4-NO$_2$)-DCit-Leu-NH—(CH$_2$)$_2$-(1-pyrrolidine);

NAcD2Nal-D4ClPhe-D3Pal-Ser-Phe(4-Atza)-DPhe(4-Atza)-Leu-NH—(CH$_2$)$_2$-(1-pyrrolidine);

NAcD2Nal-D4ClPhe-D3Pal-Ser-NMePhe(4-Atza)-DPhe(4-Atza)-Leu-NH—(CH$_2$)$_2$-(1-pyrrolidine); and NAcl)2Nal-D4ClPhe-D3Pal-Ser-Phe(4-NAc)-DPhe(4-NAc)-Leu-NH—(CH$_2$)$_2$-(1-pyrrolidine).

* * * * *

UNITED STATES PATENT AND TRADEMARK OFFICE
CERTIFICATE OF CORRECTION

PATENT NO.    : 6,191,115 B1                                             Page 1 of 1
DATED         : February 20, 2001
INVENTOR(S)   : Fortuna Haviv et al.

It is certified that error appears in the above-identified patent and that said Letters Patent is hereby corrected as shown below:

Column 28,
Line 6, replace "salt therof" with -- salt or ester thereof --
Lines 25 and 65, replace "salt ester thereof" with -- salt or ester thereof --

Column 29,
Line 2, replace "pharmaceutically acceptable carrier and compound" with
-- comprising a compound according --
Lines 6 and 10, replace "pharmaceutically acceptable carrier and compound" with
-- a compound according to --
Lines 11 and 15, replace "salt ester thereof" with -- salt or ester thereof --

Signed and Sealed this

Tenth Day of September, 2002

Attest:

JAMES E. ROGAN
Attesting Officer                    Director of the United States Patent and Trademark Office